US010301588B2

(12) United States Patent
Hoff et al.

(10) Patent No.: US 10,301,588 B2
(45) Date of Patent: May 28, 2019

(54) METHOD OF REMOVING DNA FROM BIOTECHNOLOGICAL PRODUCTS

(71) Applicant: BASF SE, Ludwigshafen (DE)

(72) Inventors: Birgit Hoff, Pfungstadt (DE); Stefan Haefner, Speyer (DE); Weol Kyu Jeong, Heidelberg (DE); Edzard Scholten, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/533,432

(22) PCT Filed: Dec. 9, 2015

(86) PCT No.: PCT/EP2015/079174
§ 371 (c)(1),
(2) Date: Jun. 6, 2017

(87) PCT Pub. No.: WO2016/091980
PCT Pub. Date: Jun. 16, 2016

(65) Prior Publication Data
US 2017/0369835 A1 Dec. 28, 2017

(30) Foreign Application Priority Data
Dec. 10, 2014 (EP) ..................................... 14197230

(51) Int. Cl.
| *C12N 1/06* | (2006.01) |
| *C12N 1/08* | (2006.01) |
| *C12P 19/34* | (2006.01) |
| *C12P 25/00* | (2006.01) |

(52) U.S. Cl.
CPC .................. *C12N 1/06* (2013.01); *C12N 1/08* (2013.01); *C12P 19/34* (2013.01); *C12P 25/00* (2013.01); *C12N 2510/00* (2013.01); *C12N 2523/00* (2013.01)

(58) Field of Classification Search
None
See application file for complete search history.

(56) References Cited

U.S. PATENT DOCUMENTS

| 4,165,250 | A | 8/1979 | Epstein et al. |
| 5,981,212 | A * | 11/1999 | Kurth ...................... C12P 25/00 435/171 |
| 8,071,365 | B2 | 12/2011 | Kroger et al. |
| 2009/0061491 | A1 | 3/2009 | Becker et al. |

FOREIGN PATENT DOCUMENTS

| CA | 2056040 A1 | 5/1992 |
| EP | 0487985 A2 | 6/1992 |
| EP | 0805201 A1 | 11/1997 |
| EP | 1529766 A1 | 5/2005 |
| JP | 2006-528150 A | 12/2006 |
| WO | WO-2005/014594 A1 | 2/2005 |
| WO | WO-2005/059144 A1 | 6/2005 |
| WO | WO-2006/131240 A2 | 12/2006 |
| WO | WO-2013/043860 A1 | 3/2013 |

OTHER PUBLICATIONS

Bretz, K., et al., "Biomass Recycling From a Riboflavin Cultivation With *B. subtilis*: Lysis, Extract Production and Testing as Substrate in Riboflavin Cultivation", Biotechnology and Bioengineering, 2006, vol. 95, No. 6, pp. 1023-1031.
Bretzel, W., et al., "Commercial Riboflavin Production by Recombinant *Bacillus subtilis*: Down-Stream Processing and Comparison of the Composition of Riboflavin Produced by Fermentation or Chemical Synthesis", Journal of Industrial Microbiology & Biotechnology, 1999, vol. 22, No. 1, pp. 19-26.
International Search Report for PCT/EP2015/079174 dated Mar. 29, 2016.
Written Opinion of the International Searching Authority for PCT/EP2015/079174 dated Mar. 29, 2016.
Canadian Office Action for Canadian Application No. 2,969,046, dated Mar. 2, 2018.

* cited by examiner

*Primary Examiner* — Christian L Fronda
(74) *Attorney, Agent, or Firm* — Drinker Biddle & Reath LLP

(57) ABSTRACT

The present invention relates to a method for degrading DNA in a sample obtained by microbial fermentation or biotransformation, comprising treating the sample with a combination of increased temperature and low pH. It also relates to a method for releasing DNA from a microbial cell, comprising incubating the microbial cell at a temperature of 45° C. to 55° C. for two to ten hours. Finally, the present invention provides a method for producing a product, comprising a step of releasing DNA from a microbial cell and degrading said DNA.

12 Claims, 5 Drawing Sheets

Specification includes a Sequence Listing.

METHOD OF REMOVING DNA FROM BIOTECHNOLOGICAL PRODUCTS

RELATED APPLICATIONS

This application is a national stage application (under 35 U.S.C. § 371) of PCT/EP2015/079174, filed Dec. 9, 2015, which claims benefit of European Application No. 14197230.7, filed Dec. 10, 2014.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074017_0035. The size of the text file is 16 KB, and the text file was created on Jun. 6, 2017.

FIELD OF THE INVENTION

The present invention relates to a method for degrading DNA in a sample obtained by microbial fermentation or biotransformation, comprising treating the sample with a combination of increased temperature and low pH. It also relates to a method for releasing DNA from a microbial cell, comprising incubating the microbial cell at a temperature of 45° C. to 55° C. for two to ten hours. Finally, the present invention provides a method for producing a product, comprising a step of releasing DNA from a microbial cell and degrading said DNA.

BACKGROUND OF THE INVENTION

In fermentation and biotransformation processes the metabolic activity of pro- and/or eukaryotic cells is used to produce substances such as beer, wine and bio-ethanol, L-glutamic-, citric- and lactic acid, different antibiotics, enzymes, steroids and aroma ingredients.

Products obtained by fermentation or biotransformation may contain DNA from the cells used in the process. On the one hand purification of intracellular products requires cell disruption upon which intracellular compounds including DNA are liberated into the broth and even after several further purification steps residual DNA may remain in the product. On the other hand also extracellular products may contain residual DNA even though an efficient separation step for cell removal is used after fermentation or biotransformation—just by cell lysis and liberation of DNA during the fermentation or biotransformation process.

For products obtained by fermentation or biotransformation and still containing DNA the regulatory requirements may be stricter than for those which do not contain residual DNA. E. g. for food and feed products obtained by fermentation of genetically modified microorganisms (GMMs) absence of GMMs and newly introduced genes in the product has a direct impact on its categorization for risk assessment purposes (EFSA (2011) The EFSA Journal 9(6): 2193). Absence of newly introduced genes should be shown by PCR spanning the full length of the coding sequence(s) of the target gene(s) of concern (EFSA (2011) The EFSA Journal 9(6): 2193).

Hence, from a regulatory point of view a reliable and cost efficient method for DNA fragmentation resulting in the absence of complete genes from the product may be of special interest.

Several approaches to achieve DNA fragmentation are known and described in the scientific literature, including enzymatic or chemical DNA degradation (Anderson (1981) Nucleic Acids Res. 9: 3015-3027; Roe (2004) Methods Mol. Biol. 255: 171-187; Bauer et al. (2003) Eur. Food Res. Technol. 217: 338-343; Poirier (2004) Nature Rev. Cancer 4: 630-637), shear forces (hydrodynamic shearing (Joneja and Huang (2009) Biotechniques 46: 553-556; Thorstenson et al. (1998) Genome Res. 8: 848-855), sonication (Deininger (1983) Anal. Biochem. 135: 247-263), nebulization (Burger et al. (2007) Nat. Protocols 2: 603-614)), oxidative attack (Aronovitch et al. (1991) Free Radic. Res. Commun. 12-13: 499-508), irradiation (Rastogi et al. (2010) Journal of Nucleic Acids; Yang and Hang (2013) J. Biomol. Tech. 24:98-103) and radicals (Dizdaroglu and Jaruga (2012) Free Radic. Res. 46:382-419).

However, for some of these methods such as the application of shear forces additional equipment is required which makes the overall process more complex and expensive. Further, when using chemical or enzymatic DNA fragmentation the enzyme or chemical compound has to be removed after the fragmentation step.

Hence, there is still a need for a simple method for removing DNA from biotechnologically produced products which does not impact product yield and product quality.

The present invention provides a method for removing DNA from biotechnologically produced products which reliably results in the absence of complete genes in the product while minimizing product losses.

SUMMARY OF THE INVENTION

The present inventors have surprisingly found that DNA can be efficiently removed from a sample obtained by microbial fermentation or biotransformation by simply changing the pH and temperature conditions of the sample.

Accordingly, the present invention provides a method of producing a product of interest with microbial cells, comprising the steps:

a) culturing the microbial cells which are capable of producing said product of interest in a culture medium;

b) disrupting the microbial cells by incubating them at a temperature of 45 to 55° C. for 2 to 10 hours, thereby releasing the DNA from the cells;

c) incubating the released DNA at a temperature of at least 50° C. and a pH of less than 4.5, thereby degrading the released DNA; and d) isolating the product of interest.

Preferably, the microbial cells are fungal cells, more preferably they are *Eremothecium gossypii* cells.

Also preferably, the product of interest is selected from the group consisting of vitamins, carotenoids, coenzymes, amino acids, organic acids, antibiotics, alcohols, terpenes, proteins, nucleotides, steroids, polysaccharides, polyhydroxyalcanoates and fatty acids, more preferably the product of interest is riboflavin.

In a particularly preferred embodiment the microbial cells are *Eremothecium gossypii* cells and the product of interest is riboflavin.

In another preferred embodiment the cells are disrupted by incubating them at a temperature of 48° C. for 4 hours.

In still a further preferred embodiment the released DNA is incubated for more than two hours and in a more preferred embodiment it is incubated at a temperature between 50° C. and 80° C. and a pH of between pH 1.0 and less than pH 4.5 for a period between more than two and ten hours.

Preferably, the disruption of step (b) and/or the incubation of step (c) is performed in fermentation broth.

Also preferably, no complete coding sequence of a gene is detectable in the product of interest isolated in step d).

In another preferred embodiment the microbial cells are genetically modified cells.

The present invention is also directed to a method for degrading DNA in a sample obtained by microbial fermentation or biotransformation, comprising incubating the sample at a temperature of at least 50° C. and a pH of less than 4.5.

Preferably, the sample obtained by microbial fermentation or biotransformation is a fermentation broth.

Also preferably, the sample is incubated for more than two hours.

In another preferred embodiment the sample is obtained by fermentation of fungal or bacterial cells or by biotransformation of a substrate using fungal or bacterial cells. More preferably, the fungal cells are *Eremothecium gossypii* cells. Also more preferably, the bacterial cells are *Bacillus subtilis* cells.

The present invention is also directed to a method for disrupting microbial cells, comprising incubating the cells at a temperature of 45 to 55° C. for 2 to 10 hours, preferably at a temperature of 48° C. for four hours.

Preferably, the microbial cells are fungal cells and more preferably *Eremothecium gossypii* cells. Most preferably, they are *Eremothecium gossypii* cells producing riboflavin.

In a further preferred embodiment, the pH is between pH 6.0 and pH 8.0, more preferably between pH 6.4 and 7.2, even more preferably between pH 6.6 and pH 7.0 and most preferably it is pH 6.8 or 6.7.

In still another embodiment the present invention is directed to a method of producing riboflavin in *Eremothecium gossypii* cells, comprising the steps:

a) culturing the cells in a culture medium;

b) disrupting the cells by incubating them at a pH of 6 to 8 and a temperature of 45 to 55° C. for 2 to 10 hours, thereby releasing the DNA from the cells;

c) incubating the released DNA at a temperature of at least 50° C. and a pH of less than 4.5, thereby degrading the DNA; and d) isolating the riboflavin.

Preferably, the cells are disrupted by incubating them at a pH of 6.8 or 6.7 and a temperature of 48° C. for 4 hours.

Also preferably, the released DNA is incubated for more than two hours and in a more preferred embodiment it is incubated at a temperature between 50° C. and 80° C. and a pH of between 2.0 and less than 4.5 for a period between more than two and ten hours. Most preferably, the released DNA is incubated for 6 hours at a temperature of 75° C. and a pH of 4.0.

Preferably, the disruption of step (b) and/or the incubation of step (c) is performed in fermentation broth.

Also preferably, no complete coding sequence of a gene is detectable in the product of interest isolated in step d).

In another embodiment the present invention relates to a method for converting a substrate into a product of interest by biotransformation using microbial cells, comprising the steps:

a) incubating a solution comprising microbial cells and the substrate for biotransformation under conditions which are suitable for biotransformation, leading to the production of the product of interest from the substrate;

b) incubating the solution of step (a) at a temperature of at least 50° C. and a pH of less than 4.5, thereby degrading any DNA present within the solution; and c) isolating the product of interest.

DETAILED DESCRIPTION OF THE INVENTION

Figure 1A:
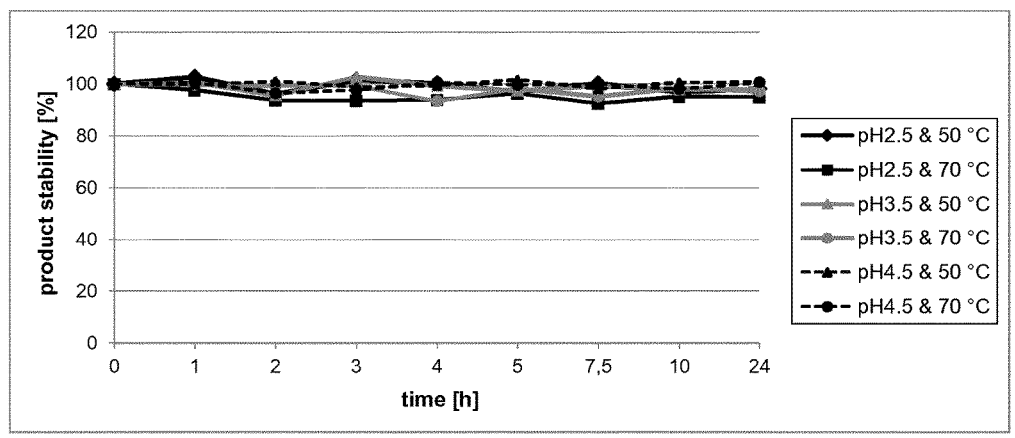
FIG. 1: Test of product stability under different pH and temperature conditions as indicated in a) and b). The product yield was measured over a period of 0 to 24 h and the starting value (0 h) was set to 100%.

Although the present invention will be described with respect to particular embodiments, this description is not to be construed in a limiting sense.

Before describing in detail exemplary embodiments of the present invention, definitions important for understanding the present invention are given. As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As discussed above, the method of the present invention involves the complete release of DNA from microbial cells and the subsequent degradation of the released DNA by a simple change in the temperature and pH conditions without the need to add additional compounds other than the pH regulating compound to effect cell disruption and/or DNA degradation. Hence, it is possible to perform the fermentation, the cell disruption and the DNA degradation in one and the same vessel without adding or removing compounds other than the pH regulating compound.

The present inventors have found that the lysis of the cells leading to a release of DNA from the microbial cell can be performed at a lower temperature as used in prior art processes. Without wishing to be bound by this theory, it is speculated that the efficient lysis of the cells is due to the remaining activity of endogenous enzymes of the cells at this lower temperature.

The inventors have further found that the DNA of the cell can be fragmented by simply changing the pH and the temperature of the fermentation broth. These conditions do not negatively influence the product titer and/or product quality.

The term "biotransformation" as used herein refers to the enzymatic conversion of a substrate to a product of interest by using enzymes produced by a microbial cell wherein the enzymes are not separated from the microbial cell producing them. The product of interest produced by biotransformation may contain DNA from the microbial cells used in the biotransformation process due to the release upon death of the microbial cells. The biotransformation process may take place in the fermentation broth or in a buffer containing the microbial cells which have been harvested from the fermentation broth, e.g. by centrifugation.

The product of interest which can be produced in the method of the present invention is any product which is commercially interesting and which is stable under the conditions used to disrupt the microbial cell and degrade the DNA, i.e. under elevated temperature and low pH.

Product classes which may be produced in the method of the present invention include, but are not limited to, vitamins, coenzymes, amino acids, organic acids, antibiotics, alcohols, terpenes, proteins and fatty acids.

Examples of vitamins which can be produced by the method of the present invention include, but are not limited to, riboflavin and vitamin B12. Coenzymes which can be produced by the method of the present invention include, but are not limited to, coenzymes Q9, Q10 and B12. Examples of amino acids which can be produced by the method of the present invention include, but are not limited to, L-methionine and L-lysine. Organic acids which can be produced by the method of the present invention include, but are not limited to, L-glutamic acid, citric acid and lactic acid. Examples of antibiotics which can be produced by the method of the present invention include, but are not limited to, penicillin, amoxicillin and streptomycin. Alcohols which can be produced by the method of the present invention include, but are not limited to, ethanol and butanol. Examples of terpenes which can be produced by the method of the present invention include, but are not limited to, monoterpenes such as myrcene, limonene and menthol, sesquiterpenes such as farnesol, selinene and patchoulol, triterpenes such as squalene and cholesterol, polyterpenes such as cis- and trans-polyisoprene, and diterpenes such as phytol and retinol. Proteins which can be produced by the method of the present invention include, but are not limited to, amylases, glucoamylases, proteases, lipases, cellulases, xylanases, mannanases, phytases, xylose isomerases, lactases, acetolactate decarboxylases, pectinases, cutinases, lyases, arabinases, galactanases, oxidases, laccase peroxidases and asparaginases. Examples of fatty acids which can be produced by the method of the present invention include, but are not limited to, eicosapentaenoic acid (EPA), hexadecanoic acid, gamma-linolenic acid (GLA), conjugated linoleic acid (CLA) and docosahexaenoic acid (DHA). Carotenoids which can be produced by the method of the present invention include, but are not limited to, β-carotene and lutein. Examples of nucleotides which can be produced by the method of the present invention include, but are not limited to, adenosine and inosine. Steroids which can be produced by the method of the present invention include, but are not limited to, cholesterol and squalene. Polysaccharides which can be produced by the method of the present invention include, but are not limited to, xanthan gum and chondroitin.

Preferably, the product of interest is a vitamin and more preferably it is riboflavin.

The term "microbial cell" is intended to include fungi, bacteria and algae

Examples of suitable bacterial cells include gram-positive bacteria and in particular bacteria from the genera *Corynebacterium, Bacillus, Clostridium, Enterococcus, Geobacillus, Lactobacillus, Lactococcus, Oceanobacillus, Staphylococcus, Streptococcus*, or *Streptomyces*, and gram-negative bacteria such as those from the genera *Campylobacter, Escherichia, Flavobacterium, Fusobacterium, Helicobacter, Ilyobacter, Neisseria, Pseudomonas, Salmonella*, or *Ureaplasma*. Particularly, suitable bacterial cells include *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus thuringi-*

*ensis, Streptococcus equisimilis, Streptococcus pyogenes, Streptococcus uberis, Streptococcus equi* subspecies *Zooepidemicus, Streptomyces murinus, Streptomyces achromogenes, Streptomyces avermitilis, Streptomyces coelicolor, Streptomyces griseus, Streptomyces lividans* strain, *Corynebacterium glutamicum* and *Escherichia coli* cells. More particularly, the bacterial cells are *Corynebacterium glutamicum* or *Bacillus subtilis* cells.

Preferably, the bacterial cells are gram-negative bacterial cells. More preferably, the bacterial cells are selected from the genera *Campylobacter, Escherichia, Flavobacterium, Fusobacterium, Helicobacter, Ilyobacter, Neisseria, Pseudomonas, Salmonella,* or *Ureaplasma.*

The fungal cell may be a yeast cell or a filamentous fungal cell, preferably it is a yeast cell.

Suitable yeast cells include *Eremothecium, Candida, Hansenula, Kluyveromyces, Pichia, Saccharomyces, Schizosaccharomyces,* and *Yarrowia* such as *Eremothecium gossypii, Saccharomyces carlsbergensis, Saccharomyces cerevisiae, Saccharomyces diastaticus, Saccharomyces douglasii, Saccharomyces kluyveri, Saccharomyces norbensis,* and *Saccharomyces oviformis.*

Suitable filamentous fungal strains include *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mortierella, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* and *Xylaria* and in particular *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturm Humicola grisea, Humicola insolens, Humicola lanuginosa, Irpex lacteus, Mortierella alpina, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* and *Trichoderma viride.*

Most preferably, the microbial cells are *Eremothecium gossypii* cells. Also most preferably, the microbial cells are *Corynebacterium glutamicum* or *Bacillus subtilis* cells.

Suitable algae may be selected from *Stramenopiles, Chrysophyceae, Xanthophyceae, Bacillariophyceae, Eugle-* *nophyceae, Cryptophyceae, Ochromonas, Nitzschia, Phaeodactylum, Skeletonema, Platymonas, Schizochytrium, Dinophyceae, Crypthecodinium, Crypthecodinium cohnii, Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia, Tetraselmis, Heteromastix longifillis, Mamiella gilva, Mantoniella squamata, Micromonas pusilla, Nephroselmis olivacea, Nephroselmis pyriformis, Nephroselmis rotunda, Ostreococcus tauri, Ostreococcus sp. Prasinocladus ascus, Prasinocladus lubricus, Pycnococcus provasolii, Pyramimonas amylifera, Pyramimonas disomata, Pyramimonas obovata, Pyramimonas orientalis, Pyramimonas parkeae, Pyramimonas spinifera, Pyramimonas sp., Tetraselmis apiculata, Tetraselmis carteriaformis, Tetraselmis chui, Tetraselmis convolutae, Tetraselmis desikacharyl, Tetraselmis gracilis, Tetraselmis hazeni, Tetraselmis impellucida, Tetraselmis inconspicua, Tetraselmis levis, Tetraselmis maculata, Tetraselmis marina, Tetraselmis striata, Tetraselmis subcordiformis, Tetraselmis suecica, Tetraselmis tetrabrachia, Tetraselmis tetrathele, Tetraselmis verrucosa, Tetraselmis verrucosa* fo. *rubens* or *Tetraselmis* sp., *Ascoglena, Astasia, Colacium, Cyclidiopsis, Euglena, Euglenopsis, Hyalophacus, Khawkinea, Lepocinclis, Phacus, Strombomonas, Trachelomonas, Euglena acus, Euglena geniculate, Euglena gracilis, Euglena mixocylindrica, Euglena rostrifera Euglena viridis, Colacium stentorium, Trachelomonas cylindrica, Trachelomonas volvocina, Porphyridium cruentum, Isochrysis galbana, Chlorella minutissima, Chlorella vulgaris, Thraustochytrium aureum, Dunaliella salina, Haematococcus pluvialis, Scenedesmus* sp. and *Nannochloropsis oculata.*

The microbial cells may be wild-type cells which are capable of producing the product of interest due to the natural presence and expression of the gene(s) required for the production of the product of interest in the genome of the cell. Alternatively, the microbial cells may be genetically modified to enable or enhance the production of the product of interest by introducing or mutating one or more genes which are involved in the production of the product of interest and/or by inhibiting the expression of one or more genes which negatively influence the production of the product of interest.

The microbial cells may be genetically modified by any techniques known in the art such as mutagenesis with chemical agents or ionizing radiation, transformation and transfection or a combination of any of these techniques. If the product of interest is riboflavin and the microbial cell is an *Eremothecium gossypii* cell, the genes which may be introduced or mutated to increase riboflavin production include, but are not limited to, the genes encoding one or more of GLY1; SHM2; ADE4; PRS 2, 4; PRS 3; MLS1; BAS1; RIB 1; RIB 2; RIB 3; RIB 4; RIB 5; RIB 7; ADE12; GUA1; Fat1; Pox1; Fox2; Pot1/Fox3; Faa 1,4 and IMPDH.

The term "culturing the microbial cell" as used herein refers to the use of any suitable means and methods known to the person skilled in the art, which allow the growth of the microbial cells and the production of the product of interest by said microbial cells.

The culturing may be performed as a batch, a repeated batch, a fed-batch, a repeated fed-batch or a continuous process.

In a fed-batch process, part of the medium or single components of the medium are fed during the fermentation process. The compounds which are selected for feeding can be fed together or separately to the fermentation process.

In a repeated fed-batch or a continuous fermentation process, the complete start medium is additionally fed during fermentation. The start medium can be fed together with or separately from the structural element feed(s). In a repeated fed-batch process, part of the fermentation broth comprising the biomass is removed at regular time intervals, whereas in a continuous process, the removal of part of the fermentation broth occurs continuously. The fermentation process is thereby replenished with a portion of fresh medium corresponding to the amount of withdrawn fermentation broth.

The culturing conditions, in particular the temperature and the pH, for a particular microbial cell can be derived from the literature. For *Eremothecium gossypii* cells, the culturing may be carried out at a temperature between 15° C. and 45° C., preferably between 20° C. and 40° C. or 15° C. and 30° C., more preferably between 20° C. and 30° C. and most preferably at 28° C. and at a pH between pH 6 and pH 9, preferably between pH 6.5 and 8.5, more preferably between 6.7 and 7.5 and most preferably between 6.8 and 7.

The culture medium contains all elements which the microbial host cell needs for growth such as a carbon source, water, various salts and a source of amino acids and nitrogen. For *Eremothecium gossypii* cells, the culture medium may comprise yeast extract, soybean flour, glycine, sodium glutamate, $KH_2PO_4$, $MgSO_4$, DL-methionine, inositol, sodium formate, urea and rapeseed or soybean oil. Suitable culture media for the cultivation of different types of microbial cells are known to the skilled expert and can be derived from the literature.

The term "fermentation broth" is intended to comprise the culture medium containing the cells after the microbial cells have been cultured.

The present invention may be useful for any production process in industrial scale, e.g., for any fermentation having culture media of at least 50 liters, preferably at least 500 liters, more preferably at least 5,000 liters, even more preferably at least 50,000 liters.

The term "disrupting the microbial cell" means that the integrity of the cell wall of the microbial cell is destroyed so that the interior of the microbial cell including the DNA is released into the medium and intact cells can no longer be detected in the culture medium. The conditions of the method of the present invention lead to a complete disruption of essentially all, i.e. more than 95 or 96%, preferably more than 97 or 98%, more preferably more than 99 or 99.5% and most preferably 100% of the microbial cells in the culture medium. Hence, this method ensures that substantially all DNA of the microbial cells is available for a subsequent degradation step.

In the method of the present invention the microbial cells are disrupted by incubating them at a temperature of 45° C. to 55° C., preferably of 46° C. to 53° C., more preferably of 47° C. to 51° C. and most preferably of 48° C. for two to ten hours, preferably for 2.5 to 8 hours, more preferably for three to eight hours, even more preferably for 3.5 to 6 hours and most preferably for four hours. Hence, the cells are incubated at a temperature of 45° C. to 55° C. for 2.5 to 8 hours, more preferably for three to eight hours, even more preferably for 3.5 to 6 hours and most preferably for four hours. The cells may also be incubated at a temperature of 46° C. to 53° C. for 2.5 to 8 hours, more preferably for three to eight hours, even more preferably for 3.5 to 6 hours and most preferably for four hours. Alternatively, the cells are incubated at a temperature of 47° C. to 51° C. for 2.5 to 8 hours, more preferably for three to eight hours, even more preferably for 3.5 to 6 hours and most preferably for four hours. Most preferably, the cells are incubated at a temperature of 48° C. for four hours.

The pH during this disruption step is preferably the same as the pH of the culture medium, as the disruption step is preferably performed in the culture step without the addition of substances in addition to those present in the culture medium. Hence, the pH during the disruption step may be in the range between pH 6.0 and pH 8.0, preferably between pH 6.2 and pH 7.6, more preferably between pH 6.4 and 7.2, even more preferably between pH 6.6 and pH 7.0 and most preferably it is pH 6.7 or 6.8. In a most preferred embodiments, the cells are incubated at a temperature of 48° C. and a pH of 6.7 for four hours to disrupt the cells.

As discussed above, the microbial cells are preferably disrupted in the fermentation broth which does not contain any compounds in addition to those used in the culturing step.

The present invention is further characterized by an efficient method for degrading DNA after it has been released from the microbial cell. This method of degrading the released DNA involves a step of incubating the released DNA at a temperature of at least 50° C., preferably at least 53° C., more preferably at least 55° C., even more preferably at least 58° C. and most preferably at a temperature of 60° C. or 65° C. or 75° C. and a pH of less than pH 4.5, preferably of less than pH 4.0, more preferably of less than pH 3.5 and most preferably of pH 3.0 or 2.5.

Hence, the method involves a step of incubating the released DNA at a temperature of at least 50° C. and a pH of less than pH 4.5, preferably of less than pH 4.0, more preferably of less than pH 3.5 and most preferably of pH 3.0 or 2.5. Alternatively, it involves a step of incubating the released DNA at a temperature of at least 53° C. and a pH of less than pH 4.5, preferably of less than pH 4.0, more preferably of less than pH 3.5 and most preferably of pH 3.0 or 2.5. In another alternative embodiment involves a step of incubating the released DNA at a temperature of at least 55° C. and a pH of less than pH 4.5, preferably of less than pH 4.0, more preferably of less than pH 3.5 and most preferably of pH 3.0 or 2.5. In still another alternative embodiment it involves a step of incubating the released DNA at a temperature of at least 58° C. and a pH of less than pH 4.5, preferably of less than pH 4.0, more preferably of less than pH 3.5 and most preferably of pH 3.0 or 2.5. In another alternative embodiment it involves a step of incubating the released DNA at a temperature of 60° C. or 65° C. and a pH of less than pH 4.5, preferably of less than pH 4.0, more preferably of less than pH 3.5 and most preferably of pH 3.0 or 2.5. In another alternative embodiment it involves a step of incubating the released DNA at a temperature of 75° C. and a pH of less than pH 4.5, preferably of less than pH 4.4, more preferably of less than pH 4.2 and most preferably of pH 4.0.

Most preferably, the released DNA is incubated at a temperature of 65° C. and a pH of pH 3.0 or at a temperature of 60° C. and a pH of pH 2.5. Also most preferably, the released DNA is incubated at a temperature of 75° C. and a pH of pH 4.0.

The temperature used within the step of incubating the released DNA is between 50° C. and 70° C., preferably between 53° C. and 68° C., more preferably between 55° C. and 67° C. and most preferably between 60° C. and 65° C. Alternatively, the temperature used within the step of incubating the released DNA is between 50° C. and 80° C., preferably between 55° C. and 78° C., more preferably between 60° C. and 77° C., even more preferably between 65° C. and 76° C. and most preferably the temperature is 75° C.

The pH used within the step of incubating the released DNA is between 1.0 and 4.5, preferably between 1.5 and 4.2, more preferably between 2.0 and 4.0, even more preferably between 2.4 and 3.8 and most preferably between 2.5 and 3.0. Alternatively, the pH used within the step of incubating the released DNA is between 2.0 and 4.5, preferably between 2.5 and 4.4, more preferably between 3.0 and 4.3, even more preferably between 3.5 and 4.2 and most preferably between 3.7 and 4.1.

The temperature used within the step of incubating the released DNA is between 50° C. and 70° C. and the pH used within the step of incubating the released DNA is between 1.0 and 4.5, preferably between 1.5 and 4.2, more preferably between 2.0 and 4.0, even more preferably between 2.4 and 3.8 and most preferably between 2.5 and 3.0. The temperature used within the step of incubating the released DNA is between 53° C. and 68° C. and the pH used within the step of incubating the released DNA is between 1.0 and 4.5, preferably between 1.5 and 4.2, more preferably between 2.0 and 4.0, even more preferably between 2.4 and 3.8 and most preferably between 2.5 and 3.0. The temperature used within the step of incubating the released DNA is between 55° C. and 67° C. and the pH used within the step of incubating the released DNA is between 1.0 and 4.5, preferably between 1.5 and 4.2, more preferably between 2.0 and 4.0, even more preferably between 2.4 and 3.8 and most preferably between 2.5 and 3.0. The temperature used within the step of incubating the released DNA is between 60° C. and 65° C. and the pH used within the step of incubating the released DNA is between 1.0 and 4.5, preferably between 1.5 and 4.2, more preferably between 2.0 and 4.0, even more preferably between 2.4 and 3.8 and most preferably between 2.5 and 3.0.

The temperature used within the step of incubating the released DNA is between 50° C. and 80° C. and the pH used within the step of incubating the released DNA is between 2.0 and 4.5, preferably between 2.5 and 4.4, more preferably between 3.0 and 4.3, even more preferably between 3.5 and 4.2 and most preferably between 3.7 and 4.1. The temperature used within the step of incubating the released DNA is between 55° C. and 78° C. and the pH used within the step of incubating the released DNA is between 2.0 and 4.5, preferably between 2.5 and 4.4, more preferably between 3.0 and 4.3, even more preferably between 3.5 and 4.2 and most preferably between 3.7 and 4.1. The temperature used within the step of incubating the released DNA is between 60° C. and 77° C. and the pH used within the step of incubating the released DNA is between 2.0 and 4.5, preferably between 2.5 and 4.4, more preferably between 3.0 and 4.3, even more preferably between 3.5 and 4.2 and most preferably between 3.7 and 4.1. The temperature used within the step of incubating the released DNA is between 65° C. and 76° C. and the pH used within the step of incubating the released DNA is between 2.0 and 4.5, preferably between 2.5 and 4.4, more preferably between 3.0 and 4.3, even more preferably between 3.5 and 4.2 and most preferably between 3.7 and 4.1.

The released DNA is incubated under the above temperature and pH conditions for a period of more than two hours, preferably more than three hours, more preferably of more than four hours, even more preferably more than five hours and most preferably for six hours.

The released DNA is incubated under the above temperature and pH conditions for a period of two to 24 hours, preferably three to 18 hours, more preferably four to twelve hours, even more preferably five to ten hours and most preferably for six hours.

The released DNA is incubated at a temperature of between 50° C. and 70° C. and a pH of between 1.0 and 4.5 for a period of two to 24 hours, preferably three to 18 hours, more preferably four to twelve hours, even more preferably five to ten hours and most preferably for six hours. The released DNA is incubated at a temperature of between 53° C. and 68° C. and a pH of between 1.5 and 4.2 for a period of two to 24 hours, preferably three to 18 hours, more preferably four to twelve hours, even more preferably five to ten hours and most preferably for six hours. The released DNA is incubated at a temperature of between 55° C. and 67° C. and a pH between 2.0 and 4.0 for a period of two to 24 hours, preferably three to 18 hours, more preferably four to twelve hours, even more preferably five to ten hours and most preferably for six hours. The released DNA is incubated at a temperature of between 60° C. and 65° C. and a pH between 2.5 and 3.0 for a period of two to 24 hours, preferably three to 18 hours, more preferably four to twelve hours, even more preferably five to ten hours and most preferably for six hours.

The released DNA is incubated at a temperature of between 50° C. and 80° C. and a pH of between 2.0 and 4.5 for a period of two to 24 hours, preferably three to 18 hours, more preferably four to twelve hours, even more preferably five to ten hours and most preferably for six hours. The released DNA is incubated at a temperature of between 55° C. and 78° C. and a pH of between 2.5 and 4.4 for a period of two to 24 hours, preferably three to 18 hours, more preferably four to twelve hours, even more preferably five to ten hours and most preferably for six hours. The released DNA is incubated at a temperature of between 60° C. and 77° C. and a pH between 3.0 and 4.3 for a period of two to 24 hours, preferably three to 18 hours, more preferably four to twelve hours, even more preferably five to ten hours and most preferably for six hours. The released DNA is incubated at a temperature of between 65° C. and 76° C. and a pH between 3.5 and 4.2 or between 3.7 and 4.1 for a period of two to 24 hours, preferably three to 18 hours, more preferably four to twelve hours, even more preferably five to ten hours and most preferably for six hours. Most preferably, the released DNA is incubated at a temperature of 75° C. and a pH of pH 4.0 for six hours.

Specific conditions which may be used for incubating the released DNA include a pH of 3.5, a temperature of 70° C. and a period of 2, 5 or 7.5 hours; a pH of 3.0, a temperature of 50° C. and a period of 5 or 10 hours; a pH of 3.0, a temperature of 60° C. and a period of 2, 4, 6 or 10 hours; a pH of 3.0, a temperature of 65° C. and a period of 2, 4, 6 or 10 hours; a pH of 3.0, a temperature of 70° C. and a period of 2, 5 or 10 hours; a pH of 2.5, a temperature of 50° C. and a period of 2, 5 or 7.5 hours; a pH of 2.5, a temperature of 60° C. and a period of 2, 4, 6 or 10 hours; a pH of 2.5, a temperature of 70° C. and a period of 2, 5 or 7.5 hours; a pH of 2.0, a temperature of 50° C. and a period of 2, 5 or 10 hours.

The pH for incubating the released DNA can be adjusted by the addition of any suitable acid, including, but not limited to, phosphoric acid, sulfuric acid, nitric acid, hydrochloric acid, hypochloric acid and acetic acid. Preferably, phosphoric acid is used to lower the pH to the values indicated above.

As discussed above, apart from the acid used to adjust the pH no further compounds are added to the released DNA during the incubation step.

The term "degrading DNA" means that the DNA present within the microbial cell is fragmented into smaller pieces so that the complete coding sequence of a gene is no longer detectable. However, it is not necessary that the DNA is degraded into the single nucleotides, as long as the complete coding sequence of a gene is no longer detectable. The presence of a complete coding sequence can be advantageously detected by amplifying the complete coding sequence in a PCR reaction using primers which bind to the start of the coding sequence and therefore comprise the ATG start codon, and to the end of the coding sequence and therefore comprise the stop codon of the gene to be analyzed. After the PCR reaction the samples may be subjected to gel electrophoresis and compared to a suitable control, such as a sample from the disrupted cell which had not been subjected to the conditions for degrading the DNA.

The method of the present invention leads to a degradation of the coding sequence of essentially all genes present within the microbial cells, i.e. the complete coding sequence of more than 90%, preferably of more than 93%, more preferably of more than 96%, even more preferably of more than 98% and most preferably 100% of all genes of the microbial cells is not detectable in a PCR reaction as described above.

The steps of disrupting the microbial cells and degrading the DNA may advantageously be performed in the fermentation broth, i.e. while the microbial cells are still present in the culture medium. Alternatively, the cells may have been subjected to one or more intermediate steps such as decanting a part of the cell culture medium, thereby providing a slurry containing the cells and the residual part of the cell culture medium, before they are disrupted and/or the DNA is degraded by the method of the present invention.

In preferred embodiments of the method of the present invention the microbial cells are disrupted by incubating them at a temperature of 47° C. to 51° C. for three to eight hours to release the DNA and the released DNA is degraded by incubating it at a temperature of at least 50° C. and a pH of less than pH 4.5, preferably of less than pH 4.0, more preferably of less than pH 3.5 and most preferably of pH 3.0 or 2.5. Also preferably, the microbial cells are disrupted by incubating them at a temperature of 45° C. to 55° C. for 2.5 to 8 hours, more preferably for three to eight hours, even more preferably for 3.5 to 6 hours and most preferably for four hours to release the DNA and the released DNA is degraded by incubating it at a temperature of at least 55° C. and a pH of less than pH4.5, preferably of less than pH 4.0, more preferably of less than pH 3.5 and most preferably of pH 3.0 or 2.5.

Most preferably, the method of the present invention for producing a product of interest comprises the steps of:
 a) culturing the microbial cells which are capable of producing said product of interest in a culture medium;
 b) disrupting the microbial cells by incubating them at a temperature of 48° C. for four hours, thereby releasing the DNA from the cells;
 c) incubating the released DNA at a temperature of 65° C. and a pH of 3.0 or at a temperature of 60° C. and a pH of 2.5 for six hours, thereby degrading the released DNA; and
 d) isolating the product of interest.

Also most preferably, the method of the present invention for producing a product of interest comprises the steps of:
 a) culturing the microbial cells which are capable of producing said product of interest in a culture medium;
 b) disrupting the microbial cells by incubating them at a temperature of 48° C. for four hours, thereby releasing the DNA from the cells;
 c) incubating the released DNA at a temperature of 75° C. and a pH of 4.0 for six hours, thereby degrading the released DNA; and
 d) isolating the product of interest.

As discussed above, the microbial cells are preferably *Eremothecium gossypii* cells and the product of interest is preferably riboflavin. Also preferably, the microbial cells are *Corynebacterium glutamicum* cells and the product of interest is preferably lysin. Also preferably, the microbial cells are *Bacillus subtilis* cells and the product of interest is preferably panthotenic acid or vitamin B2.

After degrading the DNA by the method of the present invention the product of interest may be subjected to further process steps which lead to the isolation of the product from other cell components or the cell culture medium.

The method of the present invention does not lead to a significant decrease of the product yield compared to the product yield of microbial cells which had not been treated by the method of the present invention. Hence, the product yield of samples subjected to the method of the present invention, i.e. disruption of the microbial cells and degradation of the released DNA, is at least 90%, 91% or 92%, preferably at least 93%, 94% or 95%, more preferably at least 96%, 97% or 98% and most preferably 99% or 100% of the product yield compared to samples which had not been treated by the method of the present invention.

The method for determining the product yield depends on the product of interest. The skilled person knows method for determining the product yield for each of the products listed above. For determining the riboflavin content in a sample, preferably a photometric assay may be employed which is based on a reaction of a sample obtained by the method of the present invention with a nicotinamide solution. Preferably, 250 µL of the culture are mixed with about 4.75 mL of a 40% solution of nicotinamide. Subsequently, the mixture may be incubated, e.g. for about 30 to 60 min, preferably for 40 min, at an elevated temperature, e.g. at around 60 to 80° C., preferably at about 70° C. The incubation should preferably be carried out in darkness. Subsequently, samples may be cooled, e.g. for about 5 min, and mixed with, e.g. 3 ml, water. The photometric determination of the extinction may be performed at a wavelength of 440 or 450 nm.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

Autolysis of Host Cells

A reliable method for cell killing and complete disruption of the production host *E. gossypii* after fermentation is a basic requirement for generating a fermentation broth in which the genomic DNA (gDNA) of the production host is completely liberated and therefore accessible for further treatment.

To establish well suited conditions for complete cell killing, disruption and DNA liberation, the fermentation broth was incubated for 1.5-24 h at temperatures of 45-61° C. at the end of main fermentation. Samples were taken and the cell viability was tested by CFU plating on MA2 complete medium (10 g/L Bacto peptone, 10 g/L Glucose, 1 g/L Yeast extract, 0.3 g/L Myoinosit, 20 g/L Agar).

Furthermore, the fermentation broth was separated in pellet and supernatant by centrifugation for 10 min at 15,000 rpm. About 200 mg of the pellet was resuspended in either 500 µl of $H_2O$ or 500 µl of 1× DNaseI buffer containing 50 U of DNaseI (DnaseI recombinant, RNase-free, Roche) to test if the residual gDNA was completely liberated and therefore accessible to endonuclease treatment. After incubation for 1 h at 37° C. and 500 rpm, the samples were disrupted/opened using a Ribolyser sample homogenizer and the residual gDNA was extracted from each sample (see Example 3). The extracted DNA of the +/−DNaseI treated samples was used as template in subsequent PCR analyses. PCR was done as described below (see Example 3) amplifying exemplarily the RIB5 gene (SEQ ID No.1) using the primers P1 (SEQ ID No.2)×P2 (SEQ ID No.3). The obtained PCR amplicons were analyzed via gel electrophoresis.

The results of the described analysis (see Table 1) surprisingly show that cell autolysis and gDNA liberation were more effective at lower temperatures ≤51° C. than at higher temperatures up to 56° C. since even after 15 h of incubation at 56° C. residual gDNA was detected also in the DNaseI treated samples. Under these conditions cell disruption was incomplete and therefore gDNA was still present in dead but closed cells where it was not accessible for further treatments. The best conditions for complete cell lysis and DNA liberation were at temperatures of 48-51° C. and incubation times of 3-5 h since in these samples the DNA was completely liberated from the cells and accessible for fragmentation by the DNaseI. Furthermore, the results show that residual gDNA was present in all samples without DNaseI treatment at pH6.8 even at high temperatures up to 61° C. and incubation times of up to 15 h. That means that even higher temperatures and longer incubation times alone were not sufficient for DNA fragmentation. Hence, complete autolysis and DNA liberation can be obtained at moderate pH and temperature conditions.

TABLE 1

Results of tests for efficient cell autolysis and complete DNA liberation using the amplification of the full-length open reading frame of the RIB5 gene as indicator. Complete cell disruption and DNA liberation under the conditions indicated was monitored by PCR analysis using extracted DNA +/− DNaseI treatment as template.

| | temperature | time | detection of PCR amplicon | | viable |
|---|---|---|---|---|---|
| pH | [° C.] | [h] | +DNaseI | −DNaseI | cells |
| 6.8 | 42 | 0 | + | + | + |
| 6.8 | 42 | 24 | − | + | + |
| 6.8 | 45 | 0 | + | + | + |
| 6.8 | 45 | 1.5 | − | + | + |
| 6.8 | 45 | 3 | − | + | + |
| 6.8 | 45 | 5 | − | + | + |
| 6.8 | 45 | 7.5 | − | + | − |
| 6.8 | 45 | 10 | − | + | − |
| 6.8 | 45 | 15 | − | + | − |
| 6.8 | 45 | 24 | − | + | − |
| 6.8 | 48 | 0 | + | + | + |
| 6.8 | 48 | 1.5 | + | + | + |
| 6.8 | 48 | 3 | − | + | − |
| 6.8 | 48 | 5 | − | + | − |
| 6.8 | 48 | 7.5 | − | + | − |
| 6.8 | 48 | 10 | − | + | − |
| 6.8 | 48 | 15 | − | + | − |
| 6.8 | 48 | 24 | − | + | − |
| 6.8 | 51 | 0 | + | + | + |
| 6.8 | 51 | 1.5 | + | + | − |
| 6.8 | 51 | 3 | − | + | − |
| 6.8 | 51 | 5 | − | + | − |
| 6.8 | 51 | 7.5 | − | + | − |
| 6.8 | 51 | 10 | − | + | − |
| 6.8 | 51 | 15 | − | + | − |
| 6.8 | 51 | 24 | − | + | − |
| 6.8 | 56 | 0 | + | + | + |
| 6.8 | 56 | 15 | + | + | − |
| 6.8 | 61 | 0 | + | + | + |
| 6.8 | 61 | 15 | + | + | − |

Example 2

Treatment of Fermentation Broth for Efficient DNA Fragmentation

To establish a reliable method for fragmentation of residual genomic DNA (gDNA) of the production host *E. gossypii*, the fermentation broth at the end of main cultivation was incubated for 4 h at 48° C. to kill the *E. gossypii*, disrupt the cells and liberate DNA (see Example 1). Afterwards, the pH of the autolyzed broth was decreased to values between pH4.5 to pH2 using phosphoric acid. Simultaneously, the temperature was increased to 30° C. up to 70° C. and the fermentation broth was incubated for 2 h up to 10 h. After incubation the samples were neutralized with cold sodium hydroxide.

From all these conditions samples were taken, the residual genomic DNA was extracted and analyzed via PCR for efficient DNA fragmentation (see Example 3). Furthermore, the riboflavin yield of each sample was measured (see Example 4).

Example 3

DNA Extraction of Residual gDNA and PCR Analysis to Monitor DNA Fragmentation

Any residual genomic DNA from samples generated as described above (see Example 2) was extracted using the DNeasy Plant Mini Kit (Qiagen) according to the manufacturer's recommendations with the exception that cell disruption was carried out using glass beads. For DNA extraction, 2 ml of the fermentation broth was separated in pellet and supernatant by centrifugation for 10 min at 15,000 rpm and 100 mg of the pellet or 400 µl of the supernatant was used as starting material for DNA extraction using the above mentioned kit system. The extract was then used in several PCR analyses to test for DNA absence which means rather efficient DNA fragmentation in the fermentation broth.

To this end, the total open reading frame of the terminal riboflavin biosynthesis genes RIB2 (1758 bp) and RIB4 (519 bp) were amplified. The following primer sequences were used for amplification of (i) RIB2 (SEQ ID No.4): P3 (SEQ ID No.5)×P4 (SEQ ID No.6) and (ii) RIB4 (SEQ ID No.7): P5 (SEQ ID No.8)×P6 (SEQ ID No.9). The 25 µl PCR reaction mixtures contain 12.5 µl Phusion Master Mix with GC Buffer (Thermo Scientific), 1 µl of each primer and 1 µl of the sample obtained by extraction as template. Cycle parameters were 5 min 98° C., 35 cycles of 30 s at 98° C., 30-45 s at 55-64° C., 2 min at 72° C., and a final step of 10 min at 72° C. The obtained PCR amplicons were analyzed by gel electrophoresis.

The results of the described detailed PCR analysis are summarized in Tables 2 and 3. The results show that lowering the pH and simultaneously raising the temperature leads to an efficient fragmentation of gDNA in the fermentation broth.

The full-length open reading frames of RIB2 and RIB4 can be amplified from all samples incubated at pH4.5 and a temperature from 50 up to 70° C. for ≥2 h. But the same amplicons are absent in the fermentation samples with pH values lower than 2.5. Even small fragments of 200 bp are not detectable in these samples (data not shown).

The results show that both pH decrease as well as temperature increase support gDNA fragmentation. Amplicons of the full-length RIB2 and RIB4 open reading frame are present in samples treated with pH3.0 at 30 up to 50° C. while they couldn't be detected in samples with the same pH but higher temperatures of more than 50° C.

TABLE 2

Results of the PCR analysis of the 1758 bp RIB2 gene. The fermentation broth was treated under conditions (pH, T and time) as listed below.

| pH | temperature [° C.] | incubation time [h] | detection of PCR amplicon |
|---|---|---|---|
| 6.8 | control: fermentation broth after autolysis for 4 h at 48° C. | | ++ |
| 4.5 | 50 | 2 | ++ |
| 4.5 | 50 | 5 | ++ |
| 4.5 | 50 | 7.5 | + |
| 4.5 | 70 | 2 | + |
| 4.5 | 70 | 5 | + |
| 4.5 | 70 | 7.5 | − |
| 3.5 | 50 | 2 | + |
| 3.5 | 50 | 5 | − |
| 3.5 | 50 | 7.5 | − |
| 3.5 | 70 | 2 | − |
| 3.5 | 70 | 5 | − |
| 3.5 | 70 | 7.5 | − |
| 3.0 | 30 | 2 | ++ |
| 3.0 | 30 | 5 | ++ |
| 3.0 | 30 | 10 | + |
| 3.0 | 50 | 2 | − |
| 3.0 | 50 | 5 | − |
| 3.0 | 50 | 10 | − |
| 3.0 | 60 | 2 | − |
| 3.0 | 60 | 4 | − |
| 3.0 | 60 | 6 | − |
| 3.0 | 60 | 10 | − |
| 3.0 | 65 | 2 | − |
| 3.0 | 65 | 4 | − |
| 3.0 | 65 | 6 | − |
| 3.0 | 65 | 10 | − |
| 3.0 | 70 | 2 | − |
| 3.0 | 70 | 5 | − |
| 3.0 | 70 | 10 | − |
| 2.5 | 50 | 2 | − |
| 2.5 | 50 | 5 | − |
| 2.5 | 50 | 7.5 | − |
| 2.5 | 60 | 2 | − |
| 2.5 | 60 | 4 | − |
| 2.5 | 60 | 6 | − |
| 2.5 | 60 | 10 | − |
| 2.5 | 70 | 2 | − |
| 2.5 | 70 | 5 | − |
| 2.5 | 70 | 7.5 | − |
| 2.0 | 30 | 2 | − |
| 2.0 | 30 | 5 | − |
| 2.0 | 30 | 10 | − |
| 2.0 | 50 | 2 | − |
| 2.0 | 50 | 5 | − |
| 2.0 | 50 | 10 | − |

++ indicates the detection of a PCR amplicon,
+ means a weaker PCR signal in comparison with the control at the time point zero after autolysis for 4 h at 48° C.,
− indicates no PCR amplicon detectable

TABLE 3

Results of the PCR analysis of the 519 bp RIB4 gene. The fermentation broth was treated under conditions (pH, T and time) as listed below.

| pH | temperature [° C.] | incubation time [h] | detection of PCR amplicon |
|---|---|---|---|
| 6.8 | control: fermentation broth after autolysis for 4 h at 48° C. | | ++ |
| 4.5 | 50 | 2 | ++ |
| 4.5 | 50 | 5 | ++ |
| 4.5 | 50 | 7.5 | ++ |
| 4.5 | 70 | 2 | ++ |
| 4.5 | 70 | 5 | + |
| 4.5 | 70 | 7.5 | + |
| 3.5 | 50 | 2 | ++ |
| 3.5 | 50 | 5 | + |
| 3.5 | 50 | 7.5 | + |
| 3.5 | 70 | 2 | − |
| 3.5 | 70 | 5 | − |
| 3.5 | 70 | 7.5 | − |
| 3.0 | 30 | 2 | ++ |
| 3.0 | 30 | 5 | ++ |
| 3.0 | 30 | 10 | ++ |
| 3.0 | 50 | 2 | + |
| 3.0 | 50 | 5 | − |
| 3.0 | 50 | 10 | − |
| 3.0 | 60 | 2 | − |
| 3.0 | 60 | 4 | − |
| 3.0 | 60 | 6 | − |
| 3.0 | 60 | 10 | − |
| 3.0 | 65 | 2 | − |
| 3.0 | 65 | 4 | − |
| 3.0 | 65 | 6 | − |
| 3.0 | 65 | 10 | − |
| 3.0 | 70 | 2 | − |
| 3.0 | 70 | 5 | − |
| 3.0 | 70 | 10 | − |
| 2.5 | 50 | 2 | − |
| 2.5 | 50 | 5 | − |
| 2.5 | 50 | 7.5 | − |
| 2.5 | 60 | 2 | − |
| 2.5 | 60 | 4 | − |
| 2.5 | 60 | 6 | − |
| 2.5 | 60 | 10 | − |
| 2.5 | 70 | 2 | − |
| 2.5 | 70 | 5 | − |
| 2.5 | 70 | 7.5 | − |
| 2.0 | 30 | 2 | ++ |
| 2.0 | 30 | 5 | + |
| 2.0 | 30 | 10 | − |
| 2.0 | 50 | 2 | − |
| 2.0 | 50 | 5 | − |
| 2.0 | 50 | 10 | − |

++ indicates the detection of a PCR amplicon,
+ means a weaker PCR signal in comparison with the control at the time point zero after autolysis for 4 h at 48° C.,
− indicates no PCR amplicon detectable

Example 4

Measurement of the Product Yield to Monitor Product Stability

To test the effect of pH reduction and temperature increase on product stability in the fermentation broth, samples generated as described above (see Example 2) were analysed with respect to the product yield using a photometric assay to determine the concentration of riboflavin within the samples.

250 μL of the culture were mixed with 4.75 mL of a 40% solution of nicotinamide and incubated for 40 min at 70° C. in darkness. The samples were cooled for 5 min. 40 μL of the samples were mixed with 3 mL H$_2$O and the extinction at 440 nm was measured. As blank 3 mL H$_2$O was used. The riboflavin titer was then calculated according to the following formula:

$$\text{Titer}_{Riboflavin[g/L]} = (\text{Extinction}_{[444nm]} \times M_{Riboflavin} \times \text{nicotinamide dilution} \times ((V_{cuvette} + V_{sample})/V_{sample})) / \text{molar extinction coefficient}/1000$$

$M_{riboflavin} = 376.37$ mol/L
Molar extinction coefficient=12216 L/mol/cm
Formula considering the evaporation during cultivation:

$$((25.83 - (m_{before\ incubation} - m_{after\ incubation}))/21.93) \times \text{Titer}_{riboflavin\ [g/L]}$$

Figure 1B:
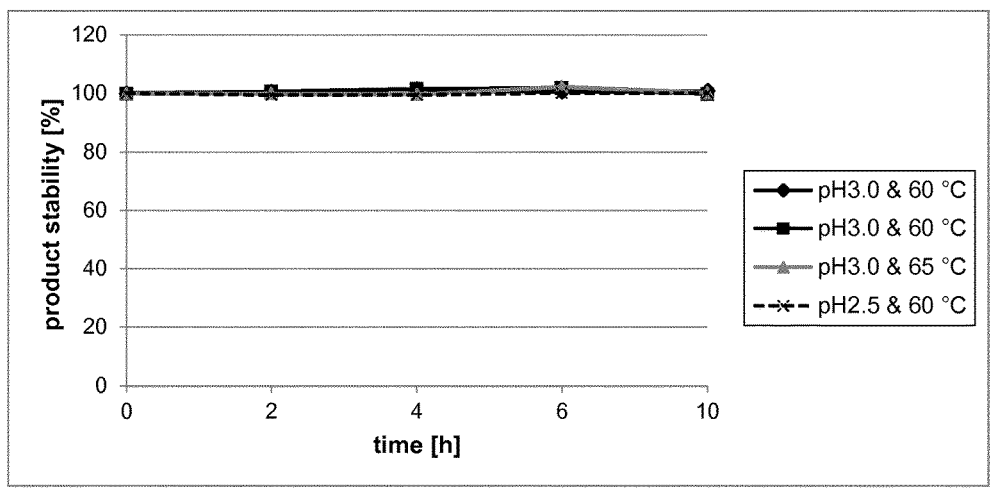
Figure 2:
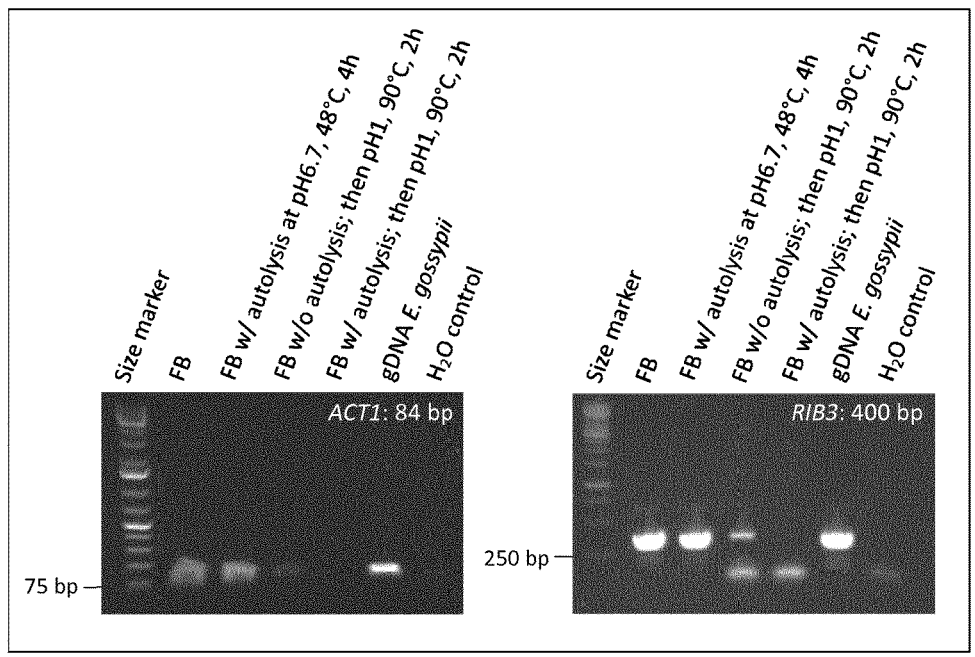
FIG. 2: Results of the PCR analysis using the 84 bp ACT1 gene fragment and the 400 bp RIB3 gene fragment. The fermentation broth (FB) was treated under the conditions (pH, T and time) as listed. The GeneRuler™ 1 kb Plus or GeneRuler™ 1 kb DNA Ladder were used as size markers.

The results of this analysis are shown in FIGS. 1 and 2. Under all conditions tested no significant changes in the riboflavin content were detectable even after incubation for ≥10 h. The product is stable under all pH and temperature conditions which were tested and which were suitable for DNA fragmentation (Example 3).

Example 5

E. gossypii Riboflavin Production in Shaking Flasks

The production of riboflavin in E. gossypii can be efficiently performed in shaking flask experiments using oil as main carbon source. 10 ml of pre-culture medium filled in 100 mL Erlenmeyer flasks without baffles was inoculated with E. gossypii mycelium (1 cm$^2$) grown for 3-4 days on SP medium plates (3 g/L Soybean flour, 3 g/L Yeast extract, 3 g/L Malt extract, 20 g/L Cornmeal, 1 g/L Antifoam, 10 g/l L Glucose, 30 g/L Agar, pH6.8). The flasks were incubated for 40 h at 30° C. and 200 rpm. 1 ml of the pre-culture was used to inoculate 24.83 mL main culture medium filled in 250 mL Erlenmeyer flasks with flat baffles. All flasks were weighed to determine the mass before incubation and then incubated for 6 days at 30° C. and 200 rpm. After growth all flasks were weighed again to determine the mass after incubation and therefore to be able to include the evaporation effect during incubation.

Pre-culture medium 55 g Yeast extract 50
0.5 g MgSO$_4$
→pH7.0 with NaOH
→filled with 950 ml H$_2$O
9.5 ml pre-culture medium+0.5 ml rapeseed oil
Main-culture medium 30 g Yeast extract 50
20 g Soybean flour
10 g Glycine
7 g Sodium glutamate
2 g KH$_2$PO$_4$
0.5 g MgSO$_4$
1.1 g DL-methionine
0.2 g Inositol
2.1 g sodium formate
→pH7.0 with NaOH
→filled with 965 ml with H$_2$O
21.2 ml main culture medium+2,8 ml rapeseed oil
→addition of 0.83 ml Urea solution
[15 g Urea/45 ml H$_2$O]

The above described cultures were analyzed concerning the riboflavin yield as described above (see Example 4). The broth from the shaking flasks was incubated for 4 h at 48° C. to achieve complete cell disruption and DNA liberation. Afterwards, the pH was decreased to pH2.5 using phosphoric acid and simultaneously the temperature was increased to 60° C. for 6 h to obtain efficient fragmentation of the genomic DNA. Subsequently, the treated broth was used to isolate the riboflavin product by further downstream processing steps.

Example 6

Combination of Autolysis and DNA-Fragmentation

Experiments with E. gossypii fermentation broth were performed to determine if DNA-fragmentation in E. gossypii works more efficient in combination with cell autolysis than without the autolysis step when using conditions with high temperatures and low pH for DNA-fragmentation.

For this purpose, fermentation broth at the end of main cultivation was taken and either incubated for cell autolysis for 4 h at 48° C. and pH 6.7 or not. Afterwards, the pH of the two samples (with and without autolysis step) was decreased to pH 1.0 using phosphoric acid. Simultaneously, the temperature was increased to 90° C. and the fermentation broth was incubated for 2 h for DNA-fragmentation. After incubation, the samples were neutralized with cold sodium hydroxide solution.

From both samples (with and without autolysis step), the riboflavin yield was measured (see Example 4) before and after incubation at 90° C., pH 1.0 for 2 h to test the effect of pH reduction, temperature increase and incubation time on product stability. The results of riboflavin measurement have shown that under the conditions tested no significant changes in the riboflavin content were detectable (data not shown).

Furthermore, to determine the DNA-fragmentation efficiency the residual genomic DNA was extracted using the DNeasy Plant Mini Kit (Qiagen) according to the manufacturer's recommendations with the exception that cell disruption was carried out using glass beads. 400 μl of the fermentation broth was used as starting material for DNA extraction. The extract was then used in several PCR analyses to test DNA-fragmentation in the fermentation broth with and without optimized cell autolysis. As controls, gDNA extracts from the untreated fermentation broth as well as from fermentation broth only after autolysis for 4 h at 48° C. and pH 6.7 were used.

For PCR analysis, a 400 bp fragment of the open reading frame of the E. gossypii RIB3 gene (SEQ ID No. 10) as well as a small 84 bp fragment of the ACT1 open reading frame (SEQ ID No. 11) were amplified. The following primer sequences were used for amplification of (i) RIB3: P9 (SEQ ID No. 12)×P10 (SEQ ID No. 13) and (ii) ACT1: P11 (SEQ ID No. 14)×P12 (SEQ ID No. 15).

The 25 μl PCR reaction mixtures contained 12.5 μl Phusion Master Mix with GC Buffer (Thermo Scientific), 5 pmol of each primer and 1 μl of the sample obtained by extraction as template. Cycle parameters were 2 min 98° C., 35-40 cycles of 30 s at 98° C., 30 s at 56-59° C., 10 s at 72° C., and a final step of 5 min at 72° C. The obtained PCR amplicons were analyzed by gel electrophoresis and the results of the described PCR analyses are summarized in FIG. 2.

The results show that an autolysis step before DNA-fragmentation significantly increases DNA-fragmentation efficiency under the DNA fragmentation conditions tested. The 84 bp ACT1 gene fragment as well as the 400 bp RIB3 gene fragment could no longer be amplified from samples with cell autolysis while both amplicons could still be obtained by PCR amplification from samples without autolysis.

Example 7

Combination of Autolysis and DNA-Fragmentation

Experiments with *E. gossypii* fermentation broth were performed to determine if DNA fragmentation in *E. gossypii* works more efficient in combination with cell autolysis than without the autolysis step using high temperatures and low pH at long incubation times for DNA fragmentation.

For this purpose, fermentation broth at the end of main cultivation was taken and either incubated for cell autolysis for 4 h at 48° C. and pH 6.7 or not. Afterwards, the pH of the two samples (with and without autolysis step) was decreased to pH 1.0 using phosphoric acid. Simultaneously, the temperature was increased to 90° C. and the fermentation broth was incubated for 10 h for DNA-fragmentation. After incubation, the samples were neutralized with cold sodium hydroxide solution.

From both samples (with and without autolysis step), the riboflavin yield was measured (see Example 4) before and after incubation at 90° C., pH 1.0 for 10 h to test the effect of pH reduction, temperature increase and incubation time on product stability. The results of riboflavin measurement showed that under the conditions tested no significant changes in the riboflavin content were detectable (data not shown).

Furthermore, to determine the DNA-fragmentation efficiency the residual genomic DNA was extracted using the DNeasy Plant Mini Kit (Qiagen) according to the manufacturer's recommendations with the exception that cell disruption was carried out using glass beads. 400 µl of the fermentation broth was used as starting material for DNA extraction. The extract was then used in several PCR analyses to test DNA-fragmentation in the fermentation broth with and without optimized cell autolysis. As controls, gDNA extracts from the untreated fermentation broth as well as from fermentation broth after autolysis for 4 h at 48° C. and pH 6.7 were used. For PCR analysis, a 113 bp and a 200 bp fragment of the open reading frame of the *E. gossypii* RIB3 gene (SEQ ID No. 10) were amplified. The following primer sequences were used for amplification of (i) RIB3 (113 bp): P13 (SEQ ID No. 16)×P14 (SEQ ID No. 17) and (ii) RIB3 (200 bp): P15 (SEQ ID No. 18)×P16 (SEQ ID No. 19).

Figure 3:
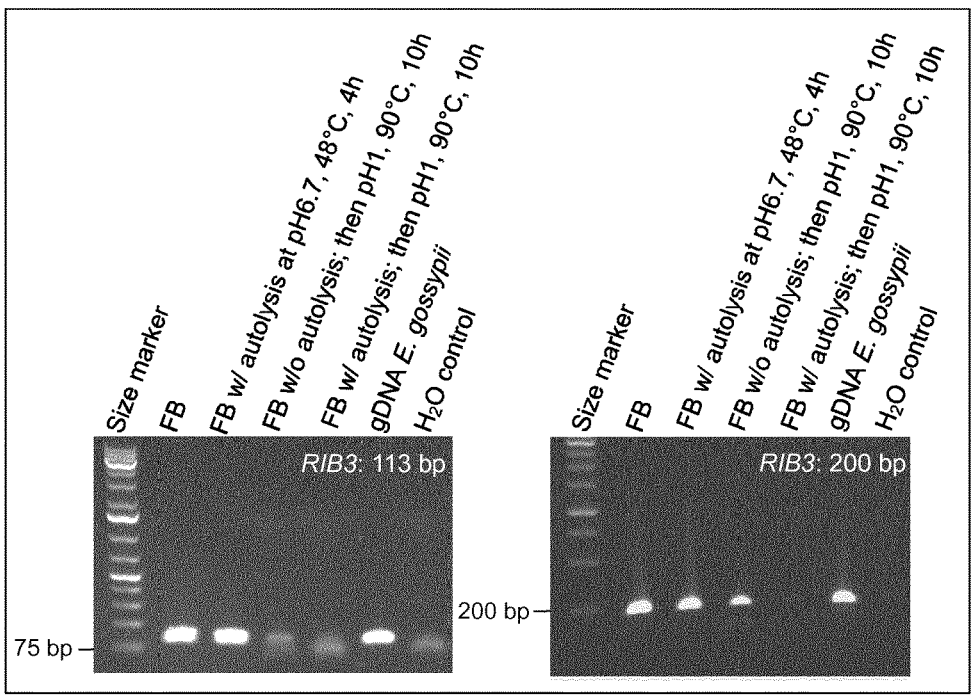
FIG. 3: Results of the PCR analysis using the 113 bp and 200 bp RIB3 gene fragments. The fermentation broth (FB) was treated under the conditions (pH, T and time) as listed. The GeneRuler™ 1 kb Plus DNA Ladder was used as size marker.

The 25 µl PCR reaction mixtures contained 12.5 µl Phusion Master Mix with GC Buffer (Thermo Scientific), 5 pmol of each primer and 1 µl of the sample obtained by extraction as template. Cycle parameters were 2 min 98° C., 35-40 cycles of 30 s at 98° C., 30 s at 57-59° C., 10 s at 72° C., and a final step of 5 min at 72° C. The obtained PCR amplicons were analyzed by gel electrophoresis and the results of the described PCR analyses are summarized in FIG. 3.

The results show that an autolysis step before DNA fragmentation significantly increases DNA fragmentation efficiency under the DNA fragmentation conditions tested. The 113 bp and 200 bp RIB3 gene fragments could no longer be amplified from samples with cell autolysis while both amplicons could still be obtained by PCR amplification from samples without autolysis.

Example 8

Combination of Autolysis and DNA-Fragmentation

Experiments with *E. gossypii* fermentation broth were performed to determine if DNA-fragmentation in *E. gossypii* works more efficient in combination with cell autolysis than without this step even using high temperatures and low pH at long incubation times for DNA fragmentation.

For this purpose, fermentation broth at the end of main cultivation was taken and either incubated for cell autolysis for 4 h at 48° C. and pH 6.7 or not. Afterwards, the pH of the two samples (with and without autolysis step) was decreased to pH 4.0 using phosphoric acid. Simultaneously, the temperature was increased to 75° C. and the fermentation broth was incubated for 6 h for DNA-fragmentation. After incubation, the samples were neutralized with cold sodium hydroxide solution.

From both samples (with and without autolysis step), the riboflavin yield was measured (see Example 4) before and after incubation at 75° C., pH 4.0 for 6 h to test the effect of pH reduction, temperature increase and incubation time on product stability. The results of riboflavin measurement showed that under the conditions tested no significant changes in the riboflavin content were detectable (data not shown).

Furthermore, to determine the DNA-fragmentation efficiency the residual genomic DNA was extracted using the DNeasy Plant Mini Kit (Qiagen) according to the manufacturer's recommendations with the exception that cell disruption was carried out using glass beads. 400 µl of the fermentation broth was used as starting material for DNA extraction. The extract was then used in several PCR analyses to test DNA-fragmentation in the fermentation broth with and without optimized cell autolysis. As controls, gDNA extracts from the untreated fermentation broth as well as from fermentation broth after autolysis for 4 h at 48° C. and pH 6.7 were used. For PCR analysis, a 200 bp fragment of the open reading frame of the *E. gossypii* RIB3 gene (SEQ ID No. 10) as well as a small 116 bp fragment of the ACT1 open reading frame (SEQ ID No. 11) were amplified. The following primer sequences were used for amplification of (i) RIB3: P15 (SEQ ID No. 18)×P16 (SEQ ID No. 19) and (ii) ACT1: P17 (SEQ ID No. 20)×P18 (SEQ ID No. 21).

Figure 4:
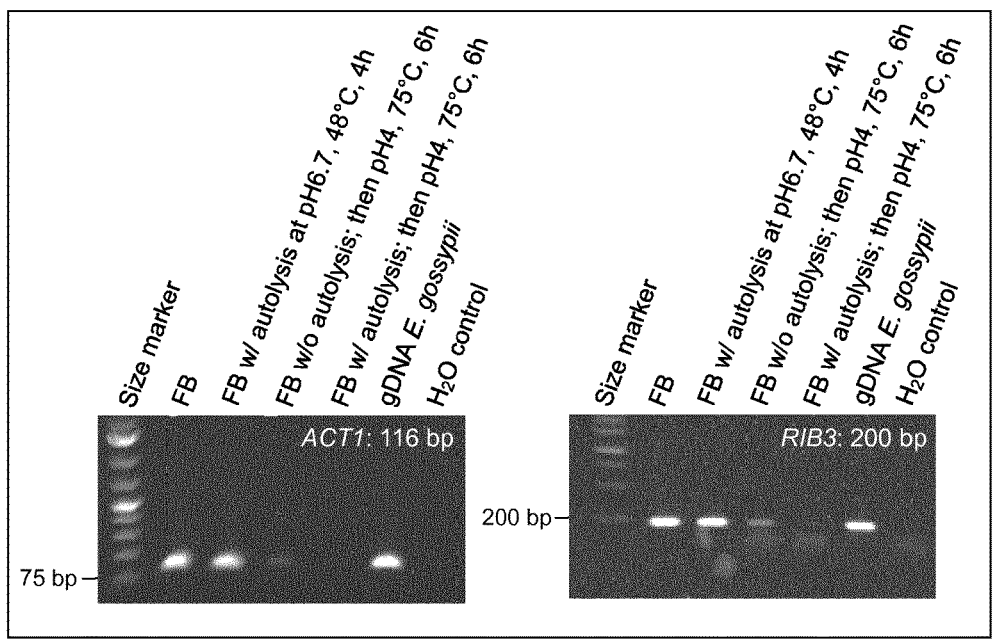
FIG. 4: Results of the PCR analysis using the 116 bp ACT1 gene fragment and the 200 bp RIB3 gene fragment. The fermentation broth (FB) was treated under the conditions (pH, T and time) as listed. The GeneRuler™ 1 kb Plus DNA Ladder was used as size marker.

The 25 µl PCR reaction mixtures contained 12.5 µl Phusion Master Mix with GC Buffer (Thermo Scientific), 5 pmol of each primer and 1 µl of the sample obtained by extraction as template. Cycle parameters were 2 min 98° C., 35-40 cycles of 30 s at 98° C., 30 s at 58-59° C., 10 s at 72° C., and a final step of 5 min at 72° C. The obtained PCR amplicons were analyzed by gel electrophoresis and the results of the described PCR analyses are summarized in FIG. 4. The results show that an autolysis step before DNA-fragmentation significantly increases DNA-fragmentation efficiency under the DNA fragmentation conditions tested. The 116 bp ACT1 gene fragment as well as the 200 bp RIB3 gene fragment could no longer be amplified from samples with cell autolysis while both amplicons could still be obtained by PCR amplification from samples without autolysis.

Example 9

Combination of Autolysis and DNA-Fragmentation

Experiments with *E. gossypii* fermentation broth were performed to determine if DNA fragmentation in *E. gossypii* works more efficient in combination with cell autolysis than without this step even using high temperatures and low pH for DNA fragmentation.

For this purpose, fermentation broth at the end of main cultivation was taken and either incubated for cell autolysis for 4 h at 48° C. and pH 6.7 or not. Afterwards, the pH of the two samples (with and without autolysis step) was decreased to pH 2.0 using phosphoric acid. Simultaneously, the temperature was increased to 90° C. and the fermentation broth was incubated for 5 min for DNA-fragmentation. After incubation, the samples were neutralized with cold sodium hydroxide solution.

From both samples (with and without autolysis step), the riboflavin yield was measured (see Example 4) before and after incubation at 90° C., pH 2.0 for 5 min to test the effect of pH reduction, temperature increase and incubation time on product stability. The results of riboflavin measurement showed that under the conditions tested no significant changes in the riboflavin content were detectable (data not shown).

Furthermore, to determine the DNA-fragmentation efficiency the residual genomic DNA was extracted using the DNeasy Plant Mini Kit (Qiagen) according to the manufacturer's recommendations with the exception that cell disruption was carried out using glass beads. 400 µl of the fermentation broth was used as starting material for DNA extraction. The extract was then used in several PCR analyses to test DNA-fragmentation in the fermentation broth with and without optimized cell autolysis. As controls, gDNA extracts from the untreated fermentation broth as well as from fermentation broth after autolysis for 4 h at 48° C. and pH 6.7 were used. For PCR analysis, a 113 bp fragment of the open reading frame of the *E. gossypii* RIB3 gene (SEQ ID No. 10) as well as a small 116 bp fragment of the ACT1 open reading frame (SEQ ID No. 11) were amplified. The following primer sequences were used for amplification of (i) RIB3: P13 (SEQ ID No. 16)×P14 (SEQ ID No. 17) and (ii) ACT1: P17 (SEQ ID No. 20)×P18 (SEQ ID No. 21).

Figure 5:
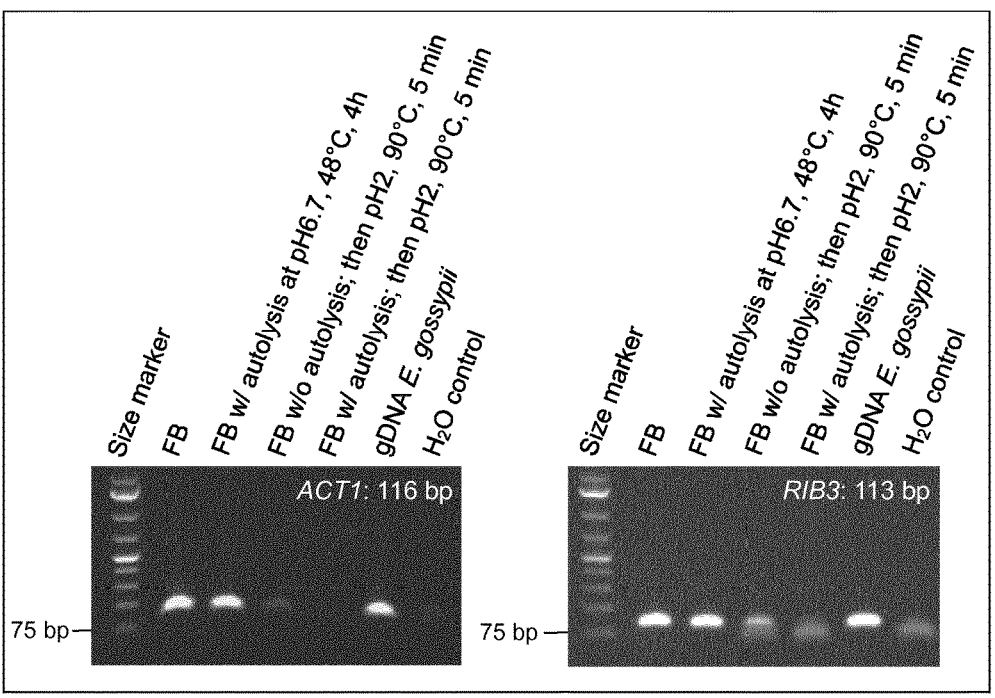
FIG. 5: Results of the PCR analysis using the 116 bp ACT1 gene fragment and the 113 bp RIB3 gene fragment. The fermentation broth (FB) was treated under the conditions (pH, T and time) as listed. The GeneRuler™1 kb Plus DNA Ladder was used as size marker.

The 25 µl PCR reaction mixtures contained 12.5 µl Phusion Master Mix with GC Buffer (Thermo Scientific), 5 pmol of each primer and 1 µl of the sample obtained by extraction as template. Cycle parameters were 2 min 98° C., 40 cycles of 30 s at 98° C., 30 s at 57-58° C., 10 s at 72° C., and a final step of 5 min at 72° C. The obtained PCR amplicons were analyzed by gel electrophoresis and the results of the described PCR analyses are summarized in FIG. 5.

The results show that an autolysis step before DNA fragmentation significantly increases DNA-fragmentation efficiency under the DNA fragmentation conditions tested. The 116 bp ACT1 gene fragment as well as the 113 bp RIB3 gene fragment could no longer be amplified from samples with cell autolysis while both amplicons could still be obtained by PCR amplification from samples without autolysis.

Example 10

Combination of Autolysis and DNA-Fragmentation

Experiments with *E. gossypii* fermentation broth were performed to determine whether the cell autolysis step alone, even at lower pH, higher temperature and long incubation time, is sufficient for efficient DNA fragmentation.

For this purpose, fermentation broth at the end of main cultivation was taken and incubated for cell autolysis at 55° C. and pH 4.0 (using phosphoric acid) for 10 h. Afterwards, one sample was treated with the DNA fragmentation step at pH 4.0, 75° C. and 6 h while one sample remained untreated. After incubation, the samples were neutralized with cold sodium hydroxide.

From both samples (±separate DNA fragmentation step), the riboflavin yield was measured (see Example 4) before and after cell autolysis and DNA fragmentation to test the effect of pH reduction, temperature increase and incubation time on product stability. The results of riboflavin measurement showed that under the conditions tested no significant changes in the riboflavin content were detectable (data not shown).

Furthermore, to determine the DNA fragmentation efficiency the residual genomic DNA was extracted using the DNeasy Plant Mini Kit (Qiagen) according to the manufacturer's recommendations with the exception that cell disruption was carried out using glass beads. 400 µl of the fermentation broth was used as starting material for DNA extraction. The extract was then used in several PCR analyses to test DNA-fragmentation in the fermentation broth with and without optimized cell autolysis. As control, gDNA extract from the untreated fermentation broth was used. For PCR analysis, the 519 bp full-length open reading frame of the RIB4 gene (SEQ ID No.7) was amplified. The following primer sequences were used for amplification of the RIB4 gene: P5 (SEQ ID No.8)×P6 (SEQ ID No.9).

Figure 6:
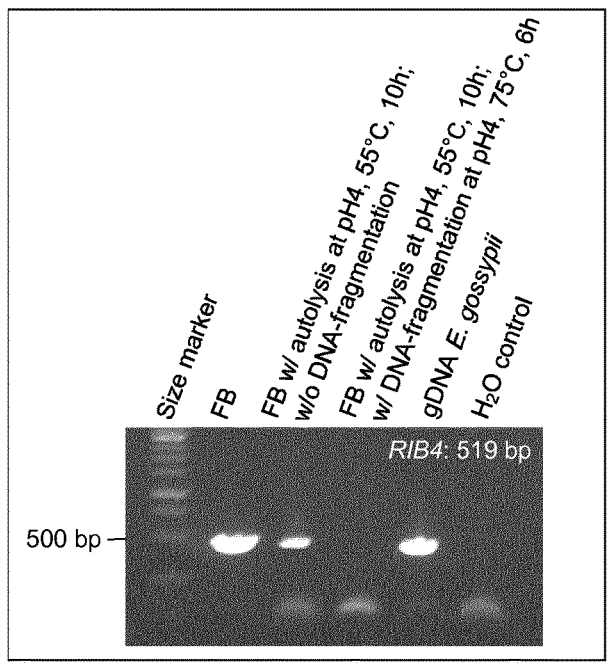
FIG. 6: Results of the PCR analysis using the 519 bp full-length open reading frame of the RIB4 gene. The fermentation broth (FB) was treated under the conditions (pH, T and time) as listed. The GeneRuler™ 1 kb DNA Ladder was used as size marker.

The 25 µl PCR reaction mixtures contained 12.5 µl Phusion Master Mix with GC Buffer (Thermo Scientific), 10 pmol of each primer and 1 µl of the sample obtained by extraction as template. Cycle parameters were 5 min 98° C., 40 cycles of 30 s at 98° C., 30 s at 58° C., 60 s at 72° C., and a final step of 10 min at 72° C. The obtained PCR amplicons were analyzed by gel electrophoresis and the results of the described PCR analyses are summarized in FIG. 6.

The results show that an autolysis step alone, even at lower pH, higher temperature and long incubation time is not sufficient for reliable DNA fragmentation. Without the subsequent DNA fragmentation step, the complete coding sequence of the RIB4 gene could still be obtained by PCR amplification. In contrast, no PCR signal could be observed by combining cell autolysis with the DNA fragmentation step as described above.

Example 11

Combination of Autolysis and DNA-Fragmentation Using *Bacillus subtilis* Cultures Experiments with *Bacillus subtilis* fermentation broth were performed to determine if DNA fragmentation in *B. subtilis* works more efficient in combination with a cell autolysis than without this step when using high temperatures and low pH for DNA fragmentation.

For this purpose, *B. subtilis* strain Marburg 168 (laboratory strain) was cultivated as follows: The fermentation process was conducted in a baffled stirred tank reactor (STR, Dasgip) with pH, $pO_2$ and temperature probes in in a medium with glucose as main carbon source and complex compounds. The concentration of $O_2$ and $CO_2$ were monitored by gas analyses. For the cultivation, the fedbatch mode was chosen with a start working volume of 1 L. As bioreactors, 2 L glass vessels were used with 3 rushton turbines with 6 blades.

Medium preparation and sterilization for seed and main culture medium took place in the shake flask and bioreactor, respectively. PPG2000 was used in all cultivations as antifoam agent. The medium contained 40 g/L complex plant protein, 5 g/L $KH_2PO_4$, 7 g/L $(NH_4)_2SO_4$, 0.09 g/L $Mn(II)SO_4*H_2O$, 0.05 g/L $Fe(II)SO_4*7H_2O$, 1 g/L $CaNO_3*4H_2O$, 2.5 mL/L PPG2000, 0.05 g/L Kanamycin. pH was adjusted to pH 6.5. The medium was sterilized in the bioreactor under stirred conditions (600 rpm) for 60 min at 123° C. The seed culture was prepared in shake flasks with the same medium as batch cultivation during a 16 h process (39° C., pH 7.5, 200 rpm). The shake flasks were inoculated from a fresh LB plate and transferred to the main culture at the end of the exponential phase after 16 h.

For inoculation of the main culture, 2.7% of the starting working volume was used. The main cultivation was conducted at 39° C., with 30 g/L start glucose concentration and pO2 dependent stirred cascade from 350-1400 rpm and an aeration rate of 1.46 vvm.

Fermentation broth at the end of main cultivation was taken and either incubated for cell autolysis or not. Cell autolysis was performed under two conditions, (i) 4 h, 48° C., pH 6.7 or (ii) 10 h, 55° C., pH 6.7. Afterwards, the pH of the three samples (2× with and 1× without autolysis step) was decreased to pH 4.0 using phosphoric acid. Simultaneously, the temperature was increased to 75° C. and the fermentation broth was incubated for 6 h for DNA-fragmentation. After incubation, the samples were neutralized with cold sodium hydroxide solution.

All samples were analyzed for DNA fragmentation efficiency by PCR analysis. To determine the DNA-fragmentation efficiency the residual genomic DNA was extracted using the DNeasy Plant Mini Kit (Qiagen) according to the manufacturer's recommendations with the exception that cell disruption was carried out using glass beads. 400 μl of the fermentation broth was used as starting material for DNA extraction. Furthermore, residual genomic DNA was extracted from 400 μl of supernatant generated by centrifugation of the fermentation broth. The extracts were then used in PCR analyses to test DNA-fragmentation with and without cell autolysis. As controls, gDNA extracts from the untreated fermentation broth as well as from fermentation broth after the cell autolysis step were used. For PCR analysis, 146 bp and 421 bp fragments of the open reading frame of the *B. subtilis* AMYE gene (SEQ ID No. 22) were amplified. The following primer sequences were used for amplification of (i) AMYE (146 bp): P19 (SEQ ID No. 23)×P20 (SEQ ID No. 24) and (ii) AMYE (421 bp): P21 (SEQ ID No. 25)×P22 (SEQ ID No. 26).

Figure 7:
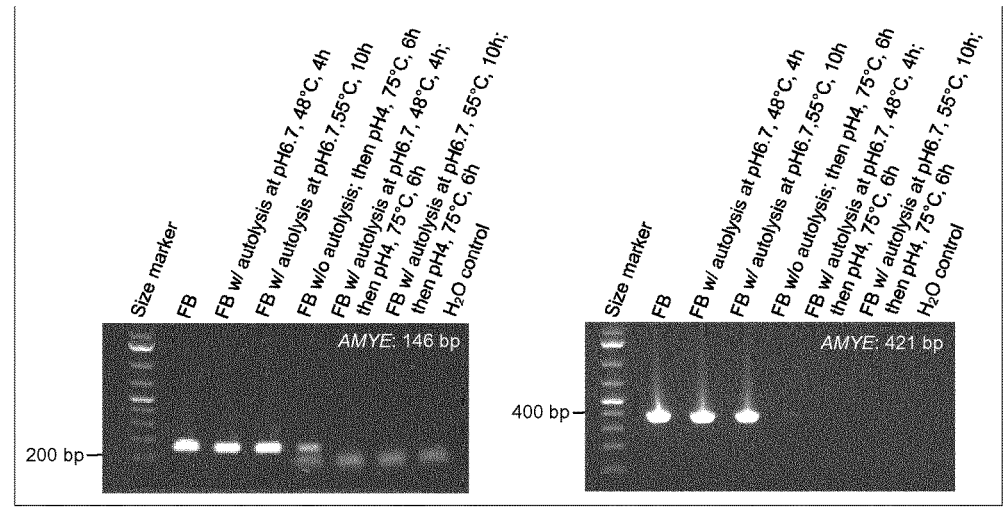
FIG. 7: Results of the PCR analysis using the 146 bp and 421 bp AMYE gene fragments from *B. subtilis*. The *B. subtilis* fermentation broth (FB) was treated under the conditions (pH, T and time) as listed. The 146 bp amplicon results from PCR analysis using supernatant gDNA extracts as template, while the 214 bp PCR fragment was obtained from PCR analysis using the DNA extraction from the complete cell suspension as template. The GeneRuler™ 1 kb Plus DNA Ladder was used as size marker.

The 25 μl PCR reaction mixtures contained 12.5 μl Phusion Master Mix with GC Buffer (Thermo Scientific), 5 pmol of each primer and 1 μl of the sample obtained by extraction as template. Cycle parameters were 2 min 98° C., 35 cycles of 30 s at 98° C., 30 s at 57° C., 15 s at 72° C., and a final step of 5 min at 72° C. The obtained PCR amplicons were analyzed by gel electrophoresis and the results of the described PCR analyses are summarized in FIG. 7.

The results show that an autolysis step before DNA fragmentation increases DNA fragmentation efficiency in *B. subtilis* fermentation broth. The 146 bp AMYE gene fragment could no longer be amplified from supernatant samples with cell autolysis while it could still be obtained by PCR amplification from samples without autolysis. Furthermore, the 421 bp AMYE-fragment is no longer detectable in the fermentation broth treated with autolysis and DNA fragmentation, but could still be observed in low amounts when the autolysis step was omitted.

Example 12

Combination of Autolysis and DNA-Fragmentation Using *Corynebacterium glutamicum* Cultures Experiments with *Corynebacterium glutamicum* cultures were performed to determine if DNA fragmentation in *C. glutamicum* works more efficient in combination with a cell autolysis step than without this step when using high temperatures and low pH for DNA fragmentation.

For this purpose, a *C. glutamicum* Lysine-producing strain ATCC13032 carrying a T311I mutation in the aspartate kinase gene ask (generated as described in Examples 1 and 2 of WO 2005/059144) was cultivated at 30° C. with vigorous shaking for 48 h using BHI plus-medium (37 g/L BHI medium (BD Biosciences), 50 ml 2M $(NH4)_2SO_4$, 100 ml 40% Glucose). Culture broth at the end of cultivation was taken and either incubated for cell autolysis or not. Cell autolysis was performed for 10 h at 55° C. and pH 6.7. Afterwards, the pH of the two samples (with and without autolysis step) was decreased to pH 4.0 using phosphoric acid. Simultaneously, the temperature was increased to 75° C. and the fermentation broth was incubated for 6 h for DNA-fragmentation. After incubation, the samples were neutralized with cold sodium hydroxide solution.

From all samples, DNA fragmentation efficiency was analyzed by PCR analysis. To determine the DNA fragmentation efficiency the residual genomic DNA was extracted using the DNeasy Plant Mini Kit (Qiagen) according to the manufacturer's recommendations with the exception that cell disruption was carried out using glass beads. 400 μl of the culture broth was used as starting material for DNA extraction. Furthermore, residual genomic DNA was extracted from 400 μl of supernatant generated by centrifugation of the culture broth. The extracts were then used in PCR analyses to test DNA-fragmentation with and without cell autolysis. As controls, gDNA extracts from the untreated culture broth as well as from culture broth after the cell autolysis step (pH 6.7, 55° C., 10 h) were used. For PCR analysis, a 212 bp fragment of the open reading frame of the *C. glutamicum* aspartate kinase gene ask (SEQ ID No. 27) were amplified using primer sequences P23 (SEQ ID No. 28)×P24 (SEQ ID No. 29).

Figure 8:
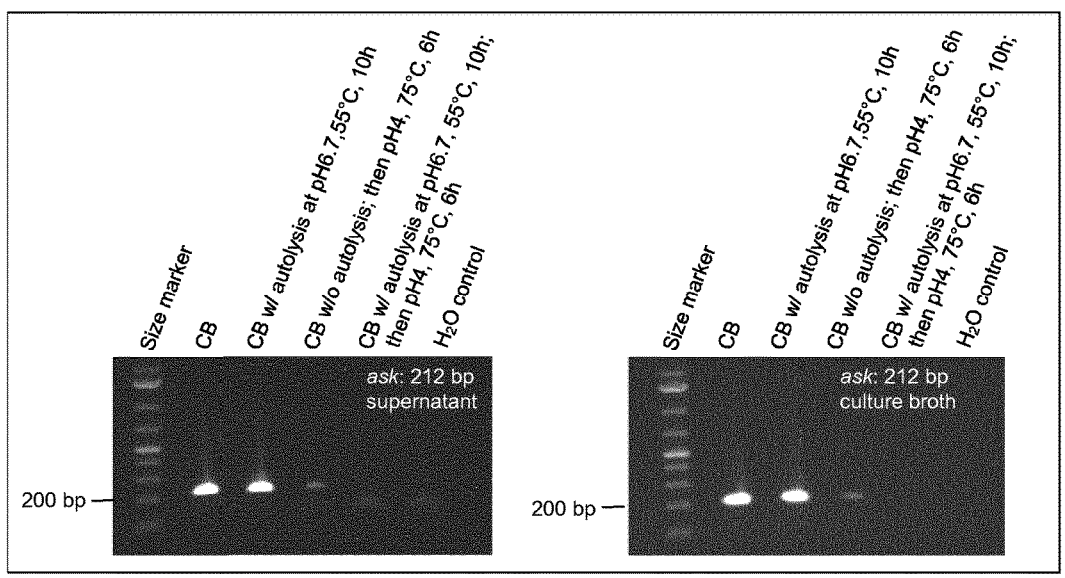
FIG. 8: Results of the PCR analysis using the 212 bp ask gene fragment from *C. glutamicum*. The *C. glutamicum* culture broth (CB) was treated under the conditions (pH, T and time) as listed. PCR analysis was done using either supernatant gDNA extracts as template or the DNA extraction from the total culture broth. The GeneRuler™ 1 kb Plus DNA Ladder was used as size marker.

The 25 μl PCR reaction mixtures contained 12.5 μl Phusion Master Mix with GC Buffer (Thermo Scientific), 5 pmol of each primer and 1 μl of the sample obtained by extraction as template. Cycle parameters were 2 min 98° C., 35 cycles of 30 s at 98° C., 30 s at 57° C., 15 s at 72° C., and a final step of 5 min at 72° C. The obtained PCR amplicons were analyzed by gel electrophoresis and the results of the described PCR analyses are summarized in FIG. 8.

The results show that an autolysis step before DNA fragmentation increases DNA-fragmentation efficiency in *C. glutamicum* culture broth. The 212 bp ask gene fragment could no longer be amplified from supernatant samples and the total culture broth treated with cell autolysis while it could still be obtained in low amounts by PCR amplification from samples without autolysis.

---

The invention claimed is:

1. A method of producing a product of interest with microbial cells, comprising:
   a) culturing microbial cells which are capable of producing a product of interest in a culture medium, wherein the product of interest is a vitamin, and the microbial cells are selected from the group consisting of *Eremothecium gossypii* and *Bacillus subtilis*;
   b) disrupting the microbial cells by incubating them at a temperature of 45 to 55° C. for 2 to 4 hours, thereby releasing the DNA from the cells;
   c) incubating the released DNA at a temperature of at least 50° C. and a pH of less than 4.5, thereby degrading the released DNA; and
   d) isolating the product of interest,
   wherein no complete coding sequence of a gene is detectable in the product of interest isolated in step d).

2. The method according to claim 1, comprising an intermediate step of decanting a part of the cell culture medium, before the DNA is degraded.

3. The method according to claim 1, wherein the microbial cells are *Bacillus subtilis* cells.

4. The method according to claim 1, wherein the product of interest is riboflavin, vitamin B12, or panthotenic acid.

5. The method according to claim 1, wherein the microbial cells are *Eremothecium gossypii* cells and the product of interest is riboflavin.

6. The method according to claim 1, wherein the cells are disrupted by incubating at a temperature of 48° C. for 4 hours.

7. The method according to claim 1, wherein the released DNA is incubated for more than two hours at a temperature of at least 50° C. and a pH of less than 4.5.

8. The method according to claim 1, wherein the released DNA is incubated at a temperature of between 50° C. and 80° C. and a pH of between pH 2.0 and pH 4.5 for a period of three to 18 hours.

9. The method according to claim 1, wherein the disruption of step (b) and/or the incubation of step (c) is performed in the culture medium.

10. The method according to claim 1, wherein the microbial cells are genetically modified cells.

11. The method according to claim 1, wherein the microbial cells are *Eremothecium gossypii* cells.

12. The method according to claim 1, wherein the product of interest is riboflavin.

* * * * *

SEQUENCE LISTING

```
<160> NUMBER OF SEQ ID NOS: 29

<210> SEQ ID NO 1
<211> LENGTH: 708
<212> TYPE: DNA
<213> ORGANISM: Eremothecium gossypii

<400> SEQUENCE: 1
atgtttaccg gtatagtgga acacattggc actgttgctg agtacttgga gaacgatgcc        60
agcgaggcag gcggcaacgg tgtgtcagtc cttatcaagg atgcggctcc gatactggcg       120
gattgccaca tcggtgactc gattgcatgc aatggtatct gcctgacggt gacggagttc       180
acggccgata gcttcaaggt cgggatcgca ccagaaacag tttatcggac ggaagtcagc       240
agctggaaag ctggctccaa gatcaaccta gaaagggcca tctcggacga caggcgctac       300
ggcgggcact acgtgcaggg ccacgtcgac tcggtggcct ctattgtatc cagagagcac       360
gacgggaact ctatcaactt taagtttaaa ctgcgcgatc aagagtacga gaagtacgta       420
gtagaaaagg gttttgtggc gatcgacggt gtgtcgctga ctgtaagcaa gatggatcca       480
gatggctgtt tctacatctc gatgattgca cacacgcaga ccgctgtagc ccttccactg       540
aagccggacg gtgccctcgt gaacatagaa acggatgtta acggcaagct agtagagaag       600
caggttgcac agtacctgaa tgcgcagctg gaaggtgaga gctcgccatt gcagcgcgtg       660
ctcgaaagga ttattgaatc caagcttgct agcatctcaa ataagtga                   708

<210> SEQ ID NO 2
<211> LENGTH: 22
<212> TYPE: DNA
<213> ORGANISM: artificial sequence
<220> FEATURE:
<223> OTHER INFORMATION: primer P1

<400> SEQUENCE: 2
atgtttaccg gtatagtgga ac                                                 22

<210> SEQ ID NO 3
<211> LENGTH: 25
<212> TYPE: DNA
<213> ORGANISM: artificial sequence
<220> FEATURE:
<223> OTHER INFORMATION: primer P2

<400> SEQUENCE: 3
tcacttattt gagatgctag caagc                                              25

<210> SEQ ID NO 4
<211> LENGTH: 1758
<212> TYPE: DNA
<213> ORGANISM: Eremothecium gossypii

<400> SEQUENCE: 4
atggaaaaca catcgcagga tgagagtcgc aaaagacagg tcgcttcgaa cttgagcagc        60
gatgccgatg agggctcgcc ggcagttacg aggccggtta aaatcaccaa cgcctcagg        120 aagaagaacc tcgggacagg cgagctacgg gacaaagcag gattcaagtt gaaggtgcaa       180
```

```
gacgtgagca aaaaccgtca cagacaggtc gatccggaat acgaagtcgt ggtagatggc      240
ccgatgcgca agatcaaacc gtatttcttc acatacaaga ctttctgcaa ggagcgctgg      300
agagatcgga agttgcttga tgtgtttgtg gatgaatttc gggaccgcga taggccttac      360
tacgagaaag tcatcggttc gggtggtgtg ctcctgaacg gtaagtcatc gacgttagat      420
agcgtattgc gtaatggaga cctcatttcg cacgagctgc accgtcatga gccaccggtc      480
tcctctaggc cgattaggac ggtgtacgaa gatgatgaca tcctggtgat tgacaagccc      540
agcgggattc cagcccatcc caccgggcgt taccgcttca actccattac gaaaatactt      600
gaaaaacagc ttggatacac tgttcatcca tgtaaccgac tggaccgcct aaccagtggc      660
ctaatgttct tggcaaaaac tccaagggga gccgatgaga tgggtgatca gatgaaggcg      720
cgcgaagtga agaaagaata tgttgcccgg gttgttgggg aatttcctat aggtgagata      780
gttgtggata tgccactgaa gactatagag ccgaagcttg ccctaaacat ggtttgcgac      840
ccggaagacg aagcgggcaa gggcgctaag acgcagctca aaagaatcag ctacgatgga      900
caaacgagca tagtcaagtg ccaaccgtac acgggccgga cgcatcagat ccgtgttcac      960
ttgcaatacc tgggcttccc aattgccaac gatccgattt attccaatcc gcacatatgg     1020
ggcccaagtc tgggcaagga atgcaaagca gactacaagg aggtcatcca aaaactaaac     1080
gaaattggta agactaaatc tgcggaaagt tggtaccatt ctgattccca aggtgaagtt     1140
ttgaaagggg aacaatgcga tgaatgtggc accgaactgt acactgaccc gggcccgaat     1200
gatcttgact tatggttgca tgcatatcgg tatgaatcca ctgaactgga tgagaacggt     1260
gctaaaaagt ggagttactc tactgcgttt cctgagtggg ctcttgagca gcacggcgac     1320
ttcatgcggc ttgccatcga acaggctaag aaatgcccac ccgcgaagac atcatttagc     1380
gttggtgccg tgttagttaa tgggaccgag attttggcca ctggttactc acgggagctg     1440
gaaggcaaca cgcacgctga acaatgtgca cttcaaaaat attttgaaca acataaaacc     1500
gacaaggttc ctattggtac agtaatatac acgactatgg agccttgttc tctccgtctc     1560
agtggtaata accgtgtgt tgagcgtata atctgccagc agggtaatat tactgctgtt      1620
tttgttggcg tacttgagcc agacaacttc gtgaagaaca atacaagtcg tgcgctattg     1680
gaacaacatg gtatagacta tattcttgtc cctgggtttc aagaagaatg tactgaagcc     1740
gcattgaagg gtcattga                                                   1758
```

<210> SEQ ID NO 5
<211> LENGTH: 26
<212> TYPE: DNA
<213> ORGANISM: artificial sequence
<220> FEATURE:
<223> OTHER INFORMATION: primer P3

<400> SEQUENCE: 5
atggaaaaca catcgcagga tgagag                                            26

<210> SEQ ID NO 6
<211> LENGTH: 24
<212> TYPE: DNA
<213> ORGANISM: artificial sequence
<220> FEATURE:
<223> OTHER INFORMATION: primer P4

<400> SEQUENCE: 6
tcaatgaccc ttcaatgcgg cttc                                              24

```
<210> SEQ ID NO 7
<211> LENGTH: 519
<212> TYPE: DNA
<213> ORGANISM: Eremothecium gossypii

<400> SEQUENCE: 7
atgattaagg gattaggcga agttgatcaa acctacgatg cgagctctgt caaggttggc      60
attgtccacg cgagatggaa caagactgtc attgacgctc tcgtccaagg tgcaattgag     120
aaactgcttg ctatgggagt gaaggagaag aatatcactg taagcaccgt tccaggtgcg     180
tttgaactac catttggcac tcagcggttt gccgagctga ccaaggcaag tggcaagcat     240 ttggacgtg tcatcccaat ggagtcctg atcaaaggcg actcaatgca ctttgaatat      300
atatcagact ctgtgactca tgccttaatg aacctacaga agaagattcg tcttcctgtc     360 attttggtt tgctaacgtg tctaacagag gaacaagcgt tgacacgtgc aggcctcggt     420
gaatctgaag gcaagcacaa ccacggtgaa gactggggtg ctgctgccgt ggagatggct     480
gtaaagtttg gcccacgcgc cgaacaaatg aagaagtga                            519

<210> SEQ ID NO 8
<211> LENGTH: 22
<212> TYPE: DNA
<213> ORGANISM: artificial sequence
<220> FEATURE:
<223> OTHER INFORMATION: primer P5

<400> SEQUENCE: 8
atgattaagg gattaggcga ag                                               22

<210> SEQ ID NO 9
<211> LENGTH: 20
<212> TYPE: DNA
<213> ORGANISM: artificial sequence
<220> FEATURE:
<223> OTHER INFORMATION: primer P6

<400> SEQUENCE: 9
tcacttcttc atttgttcgg                                                  20

<210> SEQ ID NO 10
<211> LENGTH: 639
<212> TYPE: DNA
<213> ORGANISM: Eremothecium gossypii

<400> SEQUENCE: 10
atgacaagcc catgcactga tatcggtacc gctatagagc agttcaagca aaataagatg      60
atcatcgtca tggaccacat ctcgagagaa aacgaggccg atctaatatg tgcagcagcg     120
cacatgactg ccgagcaaat ggcatttatg attcggtatt cctcgggcta cgtttgcgct     180
ccaatgacca atgcgattgc cgataagcta gacctaccgc tcatgaacac attgaaatgc     240
aaggctttct ccgatgacag acacagcact gcgtatacaa tcacctgtga ctatgcgcac     300
gggacgacga caggtatctc cgcacgtgac cgggcgttga cctgtaatca gttggcgaac     360
ccggagtcca aggctaccga cttcacgaag ccaggccaca ttgtgccatt gcgtgcccgt     420
gacggcggcg tgctcgagcg tgacgggcac accgaagcgg cgctcgactt gtgcagacta     480
gcgggtgtgc cagaggtcgc tgctatttgt gaattagtaa gcgaaaggga cgtcgggctg     540
atgatgactt tggatgagtg tatagaattc agcaagaagc acggtcttgc cctcatcacc     600
gtcgatgacc tgaaggctgc agttgccgcc aagcagtag                             639
```

<210> SEQ ID NO 11
<211> LENGTH: 1083
<212> TYPE: DNA
<213> ORGANISM: Eremothecium gossypii

<400> SEQUENCE: 11

| | | | | | |
|---|---|---|---|---|---|
| atgtgcaagg | ccggtttcgc | cggtgacgac | gctccccggg | ctgtgttccc | ttcgatcgtc | 60 |
| ggcagaccca | gacaccaggg | tatcatggtg | ggtatgggcc | agaaggactc | ctatgtgggc | 120 |
| gatgaggcgc | aatcgaagag | aggtatcttg | acgttgcgtt | acccaatcga | gcacggtatc | 180 |
| gtcacaaact | gggatgacat | ggagaagatc | tggcaccaca | cctttacaa | cgaattgaga | 240 |
| gtggccccag | aggaacaccc | agtgttgttg | acggaggcgc | ctatgaaccc | taagtcgaac | 300 |
| agagaaaaga | tgacgcagat | catgtttgaa | actttcaacg | tgcctgcctt | ctacgtgtcc | 360 |
| attcaggccg | tcttgtcgct | atactcttct | ggtagaacga | cgggtattgt | gttggactcc | 420 |
| ggtgacggtg | ttacccacgt | tgttcctatc | tacgctggtt | tctcgttgcc | acacgccatt | 480 |
| ttgagaattg | acttggccgg | cagagatatg | accgactact | tgatgaagat | ctatcggaa | 540 |
| cgtggctact | ccttttccac | cactgcagag | agagaaattg | tccgtgacat | caaagagaag | 600 |
| ctatgttacg | tcgccttgga | cttcgaacaa | gagatgcaga | ctgctgccca | gtcttcggcc | 660 |
| atcgagaagt | cctacgagct | acctgacggt | caggtgatca | ctatcggtaa | cgaaagattc | 720 |
| agagctccag | aagctttgtt | ccatccatct | gtgttgggct | tggaggctgc | cggtattgat | 780 |
| caaaccacct | acaactccat | catgaagtgt | gacgtggacg | tcagaaagga | gctctacggt | 840 |
| aacattgtga | tgtctggtgg | tactactatg | ttccctggta | tcgccgagag | aatgcagaag | 900 |
| gagatcacgg | ccttggcgcc | atcctccatg | aaggtgaaga | ttatcgctcc | accagagaga | 960 |
| aagtactccg | tctggatcgg | tggttctatc | ttggcctctc | taaccacctt | ccagcagatg | 1020 |
| tggatctcga | agcaggaata | cgatgagtct | gggccatcca | tcgttcacca | caagtgtttc | 1080 |
| taa | | | | | | 1083 |

<210> SEQ ID NO 12
<211> LENGTH: 19
<212> TYPE: DNA
<213> ORGANISM: artificial sequence
<220> FEATURE:
<223> OTHER INFORMATION: primer P9

<400> SEQUENCE: 12
gatgacagac acagcactg                                                 19

<210> SEQ ID NO 13
<211> LENGTH: 20
<212> TYPE: DNA
<213> ORGANISM: artificial sequence
<220> FEATURE:
<223> OTHER INFORMATION: primer P10

<400> SEQUENCE: 13
ctactgcttg gcggcaactg                                                20

<210> SEQ ID NO 14
<211> LENGTH: 20
<212> TYPE: DNA
<213> ORGANISM: artificial sequence
<220> FEATURE:
<223> OTHER INFORMATION: primer P11

<400> SEQUENCE: 14
gatgacgcag atcatgtttg                                              20

<210> SEQ ID NO 15
<211> LENGTH: 18
<212> TYPE: DNA
<213> ORGANISM: artificial sequence
<220> FEATURE:
<223> OTHER INFORMATION: primer P12

<400> SEQUENCE: 15
ccagaagagt atagcgac                                                18

<210> SEQ ID NO 16
<211> LENGTH: 21
<212> TYPE: DNA
<213> ORGANISM: artificial sequence
<220> FEATURE:
<223> OTHER INFORMATION: primer P13

<400> SEQUENCE: 16
tgtgaattag taagcgaaag g                                            21

<210> SEQ ID NO 17
<211> LENGTH: 18
<212> TYPE: DNA
<213> ORGANISM: artificial sequence
<220> FEATURE:
<223> OTHER INFORMATION: primer P14

<400> SEQUENCE: 17
gcagccttca ggtcatcg                                                18

<210> SEQ ID NO 18
<211> LENGTH: 17
<212> TYPE: DNA
<213> ORGANISM: artificial sequence
<220> FEATURE:
<223> OTHER INFORMATION: primer P15

<400> SEQUENCE: 18
gcagcagcgc acatgac                                                 17

<210> SEQ ID NO 19
<211> LENGTH: 20
<212> TYPE: DNA
<213> ORGANISM: artificial sequence
<220> FEATURE:
<223> OTHER INFORMATION: primer P16

<400> SEQUENCE: 19
tgcggagata cctgtcgtcg                                              20

<210> SEQ ID NO 20
<211> LENGTH: 21
<212> TYPE: DNA
<213> ORGANISM: artificial sequence
<220> FEATURE:
<223> OTHER INFORMATION: primer P17

<400> SEQUENCE: 20
gatgaagatt ctatcggaac g                                            21

<210> SEQ ID NO 21
<211> LENGTH: 20
<212> TYPE: DNA

<213> ORGANISM: artificial sequence
<220> FEATURE:
<223> OTHER INFORMATION: primer P18

<400> SEQUENCE: 21
gcatctcttg ttcgaagtcc                                                    20

<210> SEQ ID NO 22
<211> LENGTH: 1980
<212> TYPE: DNA
<213> ORGANISM: Bacillus subtilis

<400> SEQUENCE: 22

| | | | | | |
|---|---|---|---|---|---|
| atgtttgcaa | aacgattcaa | aacctcttta | ctgccgttat | tcgctggatt | tttattgctg | 60 |
| tttcatttgg | ttctggcagg | accggcggct | gcgagtgctg | aaacggcgaa | caaatcgaat | 120 |
| gagcttacag | caccgtcgat | caaaagcgga | accattcttc | atgcatggaa | ttggtcgttc | 180 |
| aatacgttaa | aacacaatat | gaaggatatt | catgatgcag | gatatacagc | cattcagaca | 240 |
| tctccgatta | ccaagtaaaa | ggaagggaat | caaggagata | aaagcatgtc | gaactggtac | 300 |
| tggctgtatc | agccgacatc | gtatcaaatt | ggcaaccgtt | acttaggtac | tgaacaagaa | 360 |
| tttaaagaaa | tgtgtgcagc | cgctgaagaa | tatggcataa | aggtcattgt | tgacgcggtc | 420 |
| atcaatcata | ccaccagtga | ttatgccgcg | atttccaatg | aggttaagag | tattccaaac | 480 |
| tggacacatg | gaaacacaca | aattaaaaac | tggtctgatc | gatgggatgt | cacgcagaat | 540 |
| tcattgctcg | ggctgtatga | ctggaataca | caaaatacac | aagtacagtc | ctatctgaaa | 600 |
| cggttcttag | acagggcatt | gaatgacggg | gcagacggtt | tcgatttga | tgccgccaaa | 660 |
| catatagagc | ttccagatga | tggcagttac | ggcagtcaat | tttggccgaa | tatcacaaat | 720 |
| acatctgcag | agttccaata | cggagaaatc | ctgcaggata | gtgcctccag | agatgctgca | 780 |
| tatgcgaatt | atatggatgt | gacagcgtct | aactatgggc | attccataag | gtccgcttta | 840 |
| aagaatcgta | atctgggcgt | gtcgaatatc | tcccactatg | catctgatgt | gtctgcggac | 900 |
| aagctagtga | catgggtaga | gtcgcatgat | acgtatgcca | atgatgatga | agagtcgaca | 960 |
| tggatgagcg | atgatgatat | ccgtttaggc | tgggcggtga | tagcttctcg | ttcaggcagt | 1020 |
| acgcctcttt | tcttttccag | acctgaggga | ggcggaaatg | gtgtgaggtt | cccggggaaa | 1080 |
| agccaaatag | cgatcgcgg | gagtgctta | tttgaagatc | aggctatcac | tgcggtcaat | 1140 |
| agatttcaca | atgtgatggc | tggacagcct | gaggaactct | cgaacccgaa | tggaaacaac | 1200 |
| cagatattta | tgaatcagcg | cggctcacat | ggcgttgtgc | tggcaaatgc | aggttcatcc | 1260 |
| tctgtctcta | tcaatacggc | aacaaaattg | cctgatggca | ggtatgacaa | taaagctgga | 1320 |
| gcgggttcat | ttcaagtgaa | cgatggtaaa | ctgacaggca | cgatcaatgc | caggtctgta | 1380 |
| gctgtgctt | atcctgatga | tattgcaaaa | gcgcctcatg | ttttccttga | gaattacaaa | 1440 |
| acaggtgtaa | cacattcttt | caatgatcaa | ctgacgatta | ccttgcgtgc | agatgcgaat | 1500 |
| acaacaaaag | ccgtttatca | aatcaataat | ggaccagaga | cggcgtttaa | ggatggagat | 1560 |
| caattcacaa | tcggaaaagg | agatccattt | ggcaaaacat | acaccatcat | gttaaaagga | 1620 |
| acgaacagtg | atggtgtaac | gaggaccgag | aaatacagtt | ttgttaaaag | agatccagcg | 1680 |
| tcggccaaaa | ccatcggcta | tcaaaatccg | aatcattgga | gccaggtaaa | tgcttatatc | 1740 |
| tataaacatg | atgggagccg | agtaattgaa | ttgaccggat | cttggcctgg | aaaaccaatg | 1800 |
| actaaaaatg | cagacggaat | ttacacgctg | acgctgcctg | cggacacgga | tacaaccaac | 1860 |
| gcaaaagtga | tttttaataa | tggcagcgcc | caagtgcccg | gtcagaatca | gcctggcttt | 1920 | gattacgtgc taaatggttt atataatgac tcgggcttaa gcggttctct tccccattga    1980

<210> SEQ ID NO 23
<211> LENGTH: 17
<212> TYPE: DNA
<213> ORGANISM: artificial sequence
<220> FEATURE:
<223> OTHER INFORMATION: primer P19

<400> SEQUENCE: 23
gtgctggcaa atgcagg                                                    17

<210> SEQ ID NO 24
<211> LENGTH: 22
<212> TYPE: DNA
<213> ORGANISM: artificial sequence
<220> FEATURE:
<223> OTHER INFORMATION: primer P20

<400> SEQUENCE: 24
gctacagacc tggcattgat cg                                              22

<210> SEQ ID NO 25
<211> LENGTH: 20
<212> TYPE: DNA
<213> ORGANISM: artificial sequence
<220> FEATURE:
<223> OTHER INFORMATION: primer P21

<400> SEQUENCE: 25
tgccgttatt cgctggattt                                                 20

<210> SEQ ID NO 26
<211> LENGTH: 20
<212> TYPE: DNA
<213> ORGANISM: artificial sequence
<220> FEATURE:
<223> OTHER INFORMATION: primer P22

<400> SEQUENCE: 26
atcgcggcat aatcactggt                                                 20

<210> SEQ ID NO 27
<211> LENGTH: 1266
<212> TYPE: DNA
<213> ORGANISM: Corynebacterium glutamicum

<400> SEQUENCE: 27
gtggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg agacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat ctttcacggg ctctcaggct     300
ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600

```
atgctggaac ttgctgctgt tggctccaag attttggtgc tgcgcagtgt tgaatacgct        660
cgtgcattca atgtgccact tcgcgtacgc tcgtcttata gtaatgatcc cggcactttg        720
attgccggct ctatggagga tattcctgtg gaagaagcag tccttaccgg tgtcgcaacc        780
gacaagtccg aagccaaagt aaccgttctg ggtatttccg ataagccagg cgaggctgcg        840
aaggttttcc gtgcgttggc tgatgcagaa atcaacattg acatggttct gcagaacgtc        900
tcttctgtag aagacggcac caccgacatc accttcacct gccctcgttc cgacggccgc        960
cgcgcgatgg agatcttgaa gaagcttcag gttcagggca actggaccaa tgtgctttac       1020
gacgaccagg tcggcaaagt ctccctcgtg ggtgctggca tgaagtctca cccaggtgtt       1080
accgcagagt tcatggaagc tctgcgcgat gtcaacgtga acatcgaatt gatttccacc       1140
tctgagattc gtatttccgt gctgatccgt gaagatgatc tggatgctgc tgcacgtgca       1200
ttgcatgagc agttccagct gggcggcgaa gacgaagccg tcgtttatgc aggcaccgga       1260
cgctaa                                                                  1266

<210> SEQ ID NO 28
<211> LENGTH: 20
<212> TYPE: DNA
<213> ORGANISM: artificial sequence
<220> FEATURE:
<223> OTHER INFORMATION: primer P23

<400> SEQUENCE: 28
ggagatcttg aagaagcttc                                                     20

<210> SEQ ID NO 29
<211> LENGTH: 20
<212> TYPE: DNA
<213> ORGANISM: artificial sequence
<220> FEATURE:
<223> OTHER INFORMATION: primer P24

<400> SEQUENCE: 29
gatcatcttc acggatcagc                                                     20
```